US009574054B2

(12) United States Patent
Jordaan et al.

(10) Patent No.: US 9,574,054 B2
(45) Date of Patent: Feb. 21, 2017

(54) EMULSION-DERIVED PARTICLES

(71) Applicant: CSIR, Pretoria (ZA)

(72) Inventors: Justin Jordaan, Germiston (ZA); Clinton Simpson, Kempton Park (ZA); Dean Brady, Midrand (ZA); Neil Stockenstrom Gardiner, Pretoria East (ZA); Isak Bartholomeus Gerber, Krugersdorp (ZA)

(73) Assignee: CSIR, Pretoria (ZA)

( * ) Notice: Subject to any disclaimer, the term of this patent is extended or adjusted under 35 U.S.C. 154(b) by 0 days.

(21) Appl. No.: 14/945,002

(22) Filed: Nov. 18, 2015

(65) Prior Publication Data

US 2016/0068641 A1    Mar. 10, 2016

Related U.S. Application Data

(63) Continuation of application No. 13/763,919, filed on Feb. 11, 2013, now abandoned, which is a continuation of application No. 12/740,123, filed as application No. PCT/IB2008/054458 on Oct. 29, 2008, now abandoned.

(30) Foreign Application Priority Data

Oct. 29, 2007   (ZA) .................................. 2007/09300

(51) Int. Cl.
| | |
|---|---|
| *C08J 3/16* | (2006.01) |
| *C08J 3/00* | (2006.01) |
| *C08J 3/24* | (2006.01) |
| *C12N 11/06* | (2006.01) |
| *C12N 11/08* | (2006.01) |
| *C07K 17/08* | (2006.01) |

(52) U.S. Cl.
CPC ................ *C08J 3/16* (2013.01); *C07K 17/08* (2013.01); *C08J 3/005* (2013.01); *C08J 3/24* (2013.01); *C12N 11/06* (2013.01); *C12N 11/08* (2013.01); *C08J 2379/02* (2013.01)

(58) Field of Classification Search
None
See application file for complete search history.

(56) References Cited

U.S. PATENT DOCUMENTS

| | | | |
|---|---|---|---|
| 4,141,857 A | 2/1979 | Levy et al. | |
| 4,415,663 A | 11/1983 | Symon et al. | |
| 4,713,333 A | 12/1987 | Chiang et al. | |
| 5,106,740 A | 4/1992 | Bader et al. | |

FOREIGN PATENT DOCUMENTS

| | | |
|---|---|---|
| EP | 0534057 B1 | 4/1997 |
| EP | 1647559 A1 | 4/2006 |
| WO | WO 02/29406 A1 | 4/2002 |

OTHER PUBLICATIONS

Poncelet et al., "Microencapsulation within crosslinked polyethyleneimine membranes." Journal of microencapsulation 11.1 (1994): 31-40.*
Ma et al. "Synthesis and surface modification of magnetic particles for application in biotechnology and biomedicine", *China Particuology* 5 (1-2):1-10 (2007).
Pieters et al. "Enzyme immobilization on a low-cost magnetic support: kinetic studies on immobilized and coimmobilized glucose oxidase and glucoamylase", *Enzyme Microb. Technol.* 14(5):361-70 (1992).
Bahulekar et al. "Polyethyleneimine in immobilization of biocatalysts", *Enzyme Microb. Technol.* 13(11):858-68 (1991).
Pulfer et al. "Incorporation of nitric oxide-releasing crosslinked polyethyleneimine microspheres into vascular grafts", *J. Biomed. Mater. Res.* 37(2):182-9 1997.
Notification of Transmittal of the International Search Report and the Written Opinion of the International Searching Authority, or the Declaration corresponding to International Application No. PCT/IB2008/054458 mailed Sep. 15, 2009.
Notification of Transmittal of the International Preliminary Report on Patentability corresponding to International Application No. PCT/IB2008/054458 mailed Feb. 4, 2010.

* cited by examiner

*Primary Examiner* — Robert Yamasaki
(74) *Attorney, Agent, or Firm* — Myers Bigel, P.A.

(57) ABSTRACT

An emulsion-derived particle comprises a lattice of polymeric strands cross-linked by means of a cross-linking agent, and interstitial openings adjacent and around the strands. Functional groups are provided on the lattice and proteins and/or modified proteins can react with these, thereby to be bonded to the lattice and hence immobilized.

9 Claims, 10 Drawing Sheets

EMULSION-DERIVED PARTICLES

CROSS REFERENCE TO RELATED APPLICATIONS

This application is a continuation application of U.S. patent application Ser. No. 13/763,919, filed on Feb. 11, 2013, which is a continuation of U.S. patent application Ser. No. 12/740,123, filed on Apr. 28, 2010, abandoned, which claims priority to PCT Application No. PCT/IB2008/054458, filed on Oct. 29, 2008, which claims priority from South African Application No. 2007/09300 filed Oct. 29, 2007, the disclosures and contents of which are incorporated by reference herein in their entirety.

FIELD OF THE INVENTION

This invention relates to emulsion-derived particles. It relates also to a process for producing such particles.

BACKGROUND OF THE INVENTION

Particles containing immobilised enzymes are typically used for biocatalysis and for diagnostics, among other applications. However, particles of which the Applicant is aware suffer from drawbacks such as inadequate surface area for sufficient enzyme immobilisation. It is thus an object of this invention to provide particles whereby this drawback is at least alleviated, and a process for producing such particles that have a high binding capacity for proteins and can immobilise the proteins.

SUMMARY OF THE INVENTION

Thus, according to a first aspect of the invention, there is provided an emulsion-derived particle, which comprises a lattice of polymeric strands cross-linked by means of a cross-linking agent, interstitial openings adjacent and around the strands, and functional groups on the lattice and with which proteins and/or modified proteins can react, thereby to be bonded to the lattice and hence immobilised.

By "emulsion-derived" is meant that the particles have been produced or formed using emulsion techniques such as, but not limited to, the emulsion based processes of the second and third aspects of the invention.

By "modified proteins" is meant proteins modified by chemical means such as by the addition of di-aldehydes, or proteins modified at a genetic level, such as by means of his-tags.

Thus, the particle includes functional groups on the polymeric strands or fibres and/or on the cross-linking agent with which proteins and/or modified proteins can react. More specifically, the functional groups may be present on the polymer of the strands or fibres, and may be selected so that bonding of the proteins and/or the modified proteins to the polymer can be effected through one or more of covalent bonding, ionic bonding, hydrophobic bonding, and affinity bonding by modifying the functional groups on the polymer.

The particle may thus include at least one protein and/or modified protein bound or bonded to the polymer by means of the functional groups, thereby being immobilised. The protein may be an enzyme or a mixture of enzymes; an antibody or a mixture of antibodies; or an antigen or a mixture of antigens or any other protein which possesses functional or structural properties. A plurality of different proteins and/or a plurality of different modified proteins can thus, if desired, be immobilised within the particle. When the protein is an enzyme, the particle provides a means whereby the optimal pH of the enzyme can be shifted to the acid or alkaline region, by immobilization of the enzyme in the particle.

When the protein and/or modified protein is covalently bonded to the polymer, this may be achieved, for example, by epoxide or aldehyde interaction with amine groups of the protein and/or the modified protein.

When the protein and/or modified protein is ionically bonded to the polymer, this may be achieved by positively or negatively charged functional groups on the polymer, ionically binding with oppositely charged amino acid residues on the protein and/or modified protein.

When the protein is hydrophobically bound to the polymer, this may be achieved by aromatic or long chain alkane hydrophobic groups on the polymer binding with hydrophobic amino acid on the protein.

When the protein is affinity bonded to the polymer, this may be achieved by affinity tags, such as divalent metals and/or avidin, binding a histidine or biotinylated protein.

The particle may naturally, if desired, contain more than one of the above types or categories of functional groups, for more efficient binding of the protein.

The polymer of the strands or fibres may be a homopolymer, and may be polyethyleneimine.

The cross-linking agent may be glutaraldehyde or another aldehyde; an epoxide; or any other suitable compound having bi or multi functional groups.

The particle may include an adjunct entrapped within the interstitial openings or spaces of the lattice. The adjunct may be selected from a co-factor, a modified co-factor, or a chemical mediator, magnetite and/or a magnetic substance. By including, in the particle, a suitable enzyme and/or a substrate as an adjunct, continuous regeneration of co-factors used in a reaction can be achieved, thereby permitting the reaction to reach equilibrium or completion. By including magnetite or a magnetic substance as an adjunct, recovery of the particles from the formation liquid medium can readily be effected, using magnetic separation.

According to a second aspect of the invention, there is provided a process for producing particles, which includes providing an emulsion of droplets of a first liquid phase dispersed in a second liquid phase, with the one liquid phase being an aqueous phase and the other being an oil phase, and with the aqueous phase containing a polymer dissolved therein as well as a cross-linking agent dissolved therein; allowing the cross-linking agent to cross-link strands of the polymer, thereby to form particles, each of which includes a lattice of strands of the polymer, cross-linked by means of the cross-linking agent, interstitial openings adjacent and around the strands, and functional groups on the lattice and with which proteins and/or modified proteins can react, thereby to be bonded to the lattice and hence immobilised.

The first liquid phase may be the aqueous phase, with the second liquid phase thus being the oil phase, so that the emulsion is a water(w)-in-oil(o) emulsion, ie a w/o emulsion. However, in other embodiments of the invention, the emulsion may be an oil-in-water (o/w) emulsion, a water-in-oil-in-water (w/o/w) emulsion, or an oil-in-water-in-oil (o/w/o) emulsion.

The emulsion may be formed by admixing a first emulsion comprising aqueous droplets, containing the polymer dissolved therein, dispersed in an oil phase, with a second emulsion comprising aqueous droplets, containing the cross-linking agent dissolved therein, dispersed in an oil phase.

According to a third aspect of the invention, there is provided a process for producing particles, which includes providing a first emulsion of droplets of a first liquid phase dispersed in a second liquid phase, with the one liquid phase being an aqueous phase and the other being an oil phase, and with the aqueous phase containing a polymer dissolved therein; combining a second emulsion of droplets of a first liquid phase dispersed in a second liquid phase, with the one liquid phase being an aqueous phase and the other being an oil phase, and with the aqueous phase containing a cross-linking agent dissolved therein, with the first emulsion; allowing the cross-linking agent to cross-link strands of the polymer, thereby to form particles, each of which includes a lattice of strands of the polymer, cross-linked by means of the cross-linking agent, interstitial openings adjacent and around the strands, and functional groups on the lattice and with which proteins and/or modified proteins can react, thereby to be bonded to the lattice and hence immobilised.

At least one of the phases may include a detergent or surfactant. The surfactant may be selected from a zwitterionic surfactant, a neutral surfactant, a charged surfactant and/or a polymeric surfactant. Anionic surfactants include an alkyl sulphate such as sodium lauryl sulphate or sodium laureth sulphate, and an alkyl ether sulphate. Cationic surfactants include centrimonium chloride. Non-ionic surfactants include ethoxylated alkyl phenol such as polyoxyethylene(10) iso-octylcyclohexyl ether (Triton X100) or polyoxyethylene(9) nonylphenyl ether (Nonoxynol-9). Zwitterionic or amphiphillic surfactants include decyl betaine. Polymeric surfactants include sorbitol-(ethylene oxide) 80, ethylene oxide-propylene oxide-ethylene oxide triblock copolymer, also known as a poloxamer, such as that available under the trade name Pluronic from BASF, and a propylene oxide-ethylene oxide-propylene oxide triblock copolymer, also known as a meroxapol.

The oil of the oil phase(s) may, at least in principal, be any suitable water immiscible organic solvent, a vegetable oil, a mineral oil, a coal or crude oil derived oily component, or a synthetic oil; however, it is preferably selected from a mineral oil, paraffin, and a solvent such as iso-octane.

As hereinbefore described, the polymer may be polyethyleneimine (PEI), while the cross-linking agent may be a difunctional or multifunctional aldehyde such as glutaraldehyde, succinaldehyde, dextran aldehyde, hexamethylene diisocyanate and glyoxal. Other suitable cross-linking agents may be used for PEI or derivitised PEI, or other polymers, such as isocyanates (including hexamethylene diisocyanate or toluene diisocyanate, or isothiocyanate); an epoxide (such as 2-chloromethyl oxirane); an anhydride; epichlorohydrin, 1-ethyl-3,3-dimethylaminopropyl carbodiimide; ethyl chloroacetate or the like. As unreacted functional groups are used for the immobilisation of the protein and/or the modified protein, the cross-linking agents may also be considered to be derivitisation agents for polymer modification or post-cross-linking modification. Other polymers or co-polymers may be used, such as polyvinyl alcohol, nylon, alginate, other proteins (such as albumin, collagen and such like) and such like, modified or otherwise.

The process may include introducing a protein, such as an enzyme, an antibody or an antigen and/or a modified protein, into and onto the particles, so that the protein and/or the modified protein react with functional groups on the polymeric strands or fibres and/or on the cross-linking agent as hereinbefore described, thereby to be bonded to the polymer of the strands or fibres and/or to the cross-linking agents, and hence immobilised.

The process may include adding an adjunct to one of the phases, so that the adjunct is entrapped within the lattices of the particles. The adjunct may further be added before or after protein linking to the lattice. As hereinbefore indicated, the adjunct may be selected from a co-factor, a modified co-factor, a chemical mediator, magnetite and/or a magnetic substance.

The process may include recovering the particles from the oil phase. In particular, the recovery of the particles may be effected by physical separation means, such as centrifugation or filtration.

The process may include drying the recovered particles. Drying of the particles may include acetone dehydration, air drying, spray drying, or, preferably, lyophilisation or vacuum drying.

The process may include adding an adjunct, as hereinbefore described, to the recovered particles before the drying of the particles, so that the adjunct becomes entrapped within the lattices of the particles.

Drying of the recovered particles may be effected, either before or after protein immobilisation, to achieve enhanced stabilization of the protein and the particles, and/or for entrapment of additives such as native or modified co-factors. Drying may also result in improved cross-linking of the proteins or modified proteins, by means of multipoint attachment. This in turn may enhance stability of proteins such as enzymes.

It is envisaged that the particles of the invention can have diverse uses or application, such as for biocatalysis, enzyme based bioremediation, diagnostics, and for binding to a surface of a solid support such as a membrane reactor or a protein immobilisation matrix, to increase its surface area.

The invention will now be described in more detail with reference to the following examples, and the accompanying drawings.

DETAILED DESCRIPTION OF THE INVENTION

Figure 1:
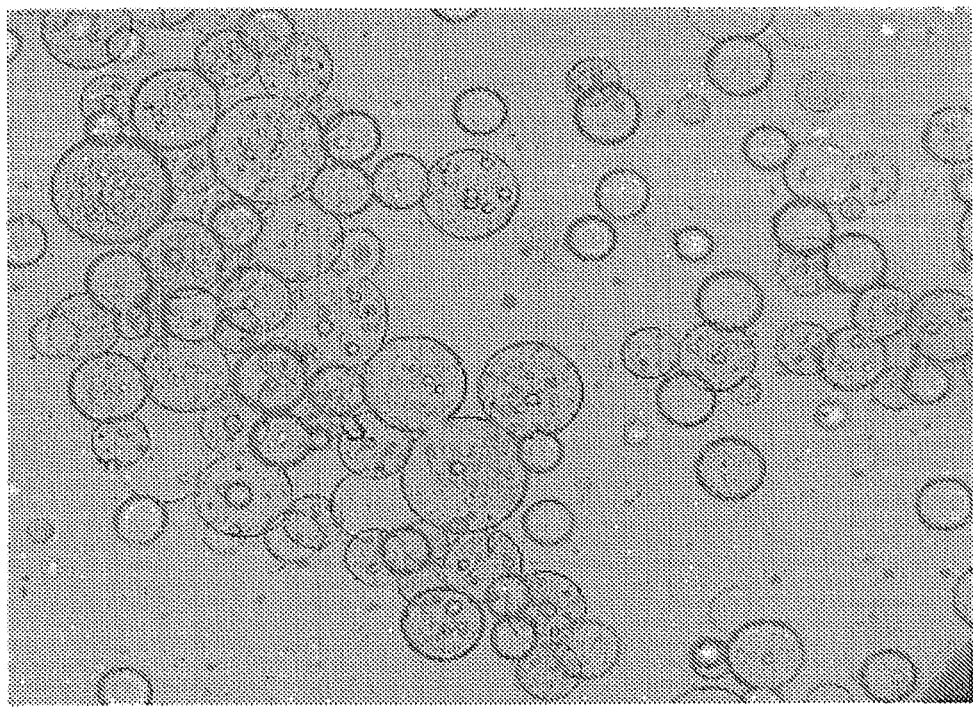
FIG. 1 is a microscopic photograph of the polymer particles of glutaraldehyde cross-linked PEI, in accordance with Example 1, showing the PEI support lattice of polymeric strands/fibres or network backbone.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Hereafter, specific embodiments of the present invention will be described in detail by way of examples. However, it should not be construed that the present invention is limited to those examples.

EXAMPLES

Example 1

Manufacturing of a Particle Consisting of a Network or Lattice of Polymeric Strands/Fibres This method involves the formation of a water-in-oil emulsion in which an emulsion containing a polyamine polymer (Polyethyleneimine) and another primary amine cross-linker (Glutaraldehyde) are combined. The two reagents react to form polymers in the form of microscopic particles or beads.

Chemicals

Glutaraldehyde (25% aqueous solution) was obtained from Acros Organics (Geel West Zone 2, Janssen Pharmaceuticalaan 3a, 2440 Geel, Belgium). Polyethyleneimine (PEI) (50% aqueous solution, Cat. No. P-3143, Mw 750,000 and Mn 60,000) was obtained from Sigma-Aldrich (St Louis, Mo. 63178). Mineral oil (white oil medicinal, 48031) was purchased from Castrol (8 Junction Avenue, Parktown, 2193 Johannesburg, South Africa).

Method for Making Particles

Emulsion A Composition 10 ml mineral oil (oil phase)

0.05 ml nonoxyol-4 (surfactant)

0.5 ml Polyethyleneimine (polyamine), (10% m/v aqueous solution), pH 11

Stirred at 700 rpm, 30 min using a magnetic stirrer.

Emulsion B Composition 10 ml mineral oil (oil phase)

0.05 ml nonoxyol-4 (surfactant)

0.5 ml glutaraldehyde, (25% m/v, grade II)

Stirred at 700 rpm, 30 min using a magnetic stirrer.

The two emulsions (A and B) were combined to permit the polymer cross-linking reaction and stirred using a magnetic stirrer bar at 700 rpm for 30 minutes to 1 hour to ensure the maintenance of the emulsion. The emulsion was then centrifuged at 3000 rpm (10 minutes in a Beckman-Coulter J2-21ME fitted with a JA20.1 rotor) to recover the particles formed. The pellet was re-suspended in deionised water, diluted to 10 to 40 ml, and then centrifuged again. This washing process was repeated twice more. The final supernatant was clear. The final pellet was suspended in 10 ml of Tris-Cl buffer (0.05 M, pH 8.0).

Results

Material from all emulsion preparations was recovered by centrifugation and visualized by light microscopy. The result of lattice formation is shown in FIG. 1, indicating that roughly spherical particles were formed.

Influence of the PEI: Glutaraldehyde Concentration Ratio on Particle Formation

The influence of the ratio of PEI to glutaraldehyde on particle formation was investigated. Samples were prepared according to Table 1.

Dry weight determination was performed by lyophilisation of the fibrous backbone lattice or support and weighing. The results of this experiment are tabulated in Table 1, and indicate that a wide range of reactant combinations form particles.

TABLE 1

Quantities of PEI and Glutaraldehyde used for fibrous polymeric backbone manufacture evaluation.

| Sample | PEI (% of aqueous) | Glutaraldehyde (% of aqueous) | Backbone Dry Weight (mg) |
|---|---|---|---|
| A | 5 | 12.5 | 36 |
| B | 4.5 | 12.5 | 43.4 |
| C | 4 | 12.5 | 40.2 |
| D | 3.5 | 12.5 | 38.2 |
| E | 3 | 12.5 | 27.2 |
| F | 2.5 | 12.5 | 20.4 |
| G | 5 | 10 | 40.8 |
| H | 5 | 7.5 | 37.8 |
| I | 5 | 5 | 36.6 |
| J | 5 | 2.5 | 35.4 |

Example 2

Binding of Laccase to PEI Support Lattice of Polymeric Strands/Fibres or Network Backbone Enzymes DeniLite™, a laccase, was obtained from Novozymes (Novozymes NS, Krogshoejvej 36, 2880 Bagsvaerd, Denmark).

Enzyme Washing

Laccase was partially purified from DeniLite™ by dissolving 5 g DeniLite II Base in 100 ml double distilled $H_2O$, while stirring at 200 rpm for 1 hour at 4° C. Suspended solids were removed by centrifugation at 10000 rpm for 1 hour at 4° C. using a JA14 rotor in a Beckman-Coulter J2-21 ME centrifuge. The supernatant was removed and dialyzed against 3 changes of 5 l of water at 4° C. using SnakeSkin™ (Pierce) dialysis tubing with a 10 kDa cut-off. The first two changes lasted for 2 hours and the final dialysis for 12 hours. The enzyme was frozen in liquid nitrogen and lyophilized. This laccase was then stored at 4° C. until required.

Laccase Assays

Laccase assays were performed on centrifugal supernatants after binding laccase to the support and the support immobilised laccase to determine activity maintenance on binding. Laccase reagent contained 1 mM guaiacol as the substrate in 100 mM succinate-lactate buffer (pH 4.5) (Jordaan J, Pletschke B, Leukes W. 2004 Purification and partial characterization of a thermostable laccase from an unidentified basidiomycete. Enz. Microb. Technol. 34:635-641). Assays were performed in triplicate at 450 nm with an extinction coefficient of 5 200 $M^{-1} \cdot cm^{-1}$. Assays were performed using a PowerWave HT Microtitre plate reader. One unit of enzyme was defined as the quantity of enzyme required to oxidise 1 µmol of substrate per minute.

Protein Determination

Protein loading was followed by determining the protein concentration in solution by means of light absorbance at 280 nm with laccase as the standard protein. Bound protein was defined as total protein minus residual protein in solution.

Enzyme Immobilisation

Enzyme, laccase (1 ml of a 10 mg·$ml^{-1}$ solution) was bound to the support by mild agitation for 30 minutes at room temperature. Enzyme was bound to the backbone dry weight indicated in Table 2. Particles with bound laccase were recovered by centrifugation at 700×g for 5 minutes. The immobilised enzyme was washed 5 times with 50 ml water and recovered through the aforementioned centrifugation.

Protein, in this case the enzyme laccase, was added to the PEI-glutaraldehyde particles (derivatised or otherwise) in the form of a buffer solution. Particles were prepared as described in Example 1. The particles were allowed to react with the protein to permit immobilisation of the protein to the polymer as mentioned above. The particles had not been dried after recovery by centrifugation and before use.

Figure 2:
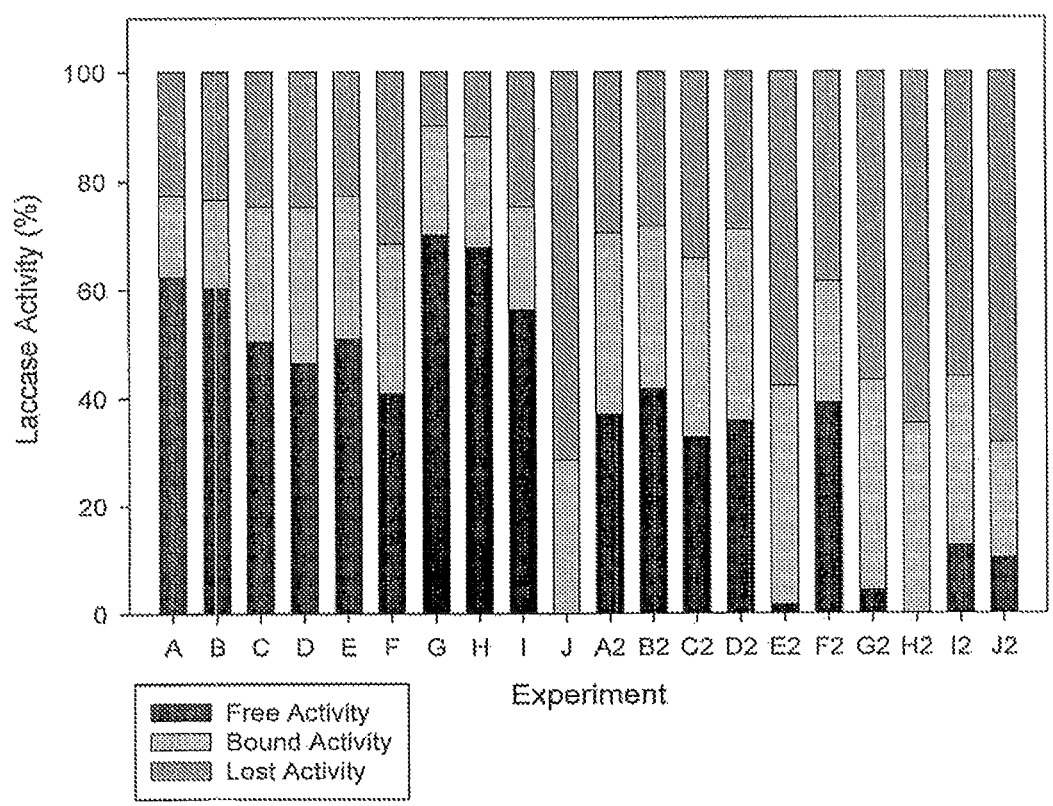
FIG. 2 is a graph which illustrates the results obtained for laccase binding to fibrous lattices, in accordance with Example 2, with binding efficiencies corrected for pH profile shifting.

The results for protein binding to the various manufactured protein supports are tabulated below (Table 2), while results for laccase activity are indicated in FIG. 2.

Results

TABLE 2

Binding efficiency of laccase onto backbone support

| Sample | PEI (mg) | Glutaraldehyde (mg) | Backbone Dry Weight (mg) | Bound Protein (mg) | Protein Loading (mg · $g^{-1}$) |
|---|---|---|---|---|---|
| A | 5 | 12.5 | 36 | 3.24 | 89.89 |
| B | 4.5 | 12.5 | 43.4 | 4.95 | 137.43 |
| C | 4 | 12.5 | 40.2 | 5.50 | 152.83 |
| D | 3.5 | 12.5 | 38.2 | 5.96 | 165.45 |
| E | 3 | 12.5 | 27.2 | 6.62 | 183.85 |
| F | 2.5 | 12.5 | 20.4 | 6.34 | 176.05 |
| G | 5 | 10 | 40.8 | 6.22 | 172.67 |
| H | 5 | 7.5 | 37.8 | 5.66 | 157.27 |
| I | 5 | 5 | 36.6 | 5.03 | 139.70 |
| J | 5 | 2.5 | 35.4 | 9.43 | 261.93 |

Another experimental set was prepared as in Table 1; however, in this example the particles were post-treated with glutaraldehyde and designated by the number two (i.e. A2-J2). Laccase was subsequently bound to the particle according to the method described above. Particles with bound laccase were recovered by centrifugation at 700×g for 5 minutes.

The results for enzyme activity loaded onto the polymeric support are indicated in FIG. 2.

This research indicates that the fibrous lattice or network may be used as a protein immobilisation support with high protein binding capacity while retaining functional activity of the protein.

Example 3

Manufacture of PEI Support Lattice of Polymeric Strands/Fibres or Network Backbone Using Various Oils The influence of variation in the oil phase of the emulsion was investigated. The particles were manufactured by initially preparing 2 separate emulsions A and B.

Emulsion A Composition 10 ml mineral oil, paraffin oil, or isooctane (oil phase)
0.1 ml nonoxyol-4 (surfactant)
0.5 ml Polyethyleneimine (polyamine), (10% m/v aqueous solution), pH 11.
Stirred at 500 rpm, 25° C., 30 min using a magnetic stirrer.

Emulsion B Composition 10 ml same oil phase as above.
0.1 ml nonoxyol-4 (surfactant)
0.5 ml glutaraldehyde, (25% m/v, grade 10,
Stirred at 500 rpm, 25° C., 30 min using a magnetic stirrer.

Thereafter emulsion A was quickly added to emulsion B and stirred for a further hour (700 rpm). The particles were recovered from the emulsions by centrifugation (3000×g, Sorvall benchtop centrifuge) for 10 minutes followed by washing 6 fold with 10 ml volumes of deionised water. After washing the final particles were resuspended to 20 ml in deionised water, half of which was dried by lyophilisation. Both the wet and dried particles were analysed for particle size distribution (Malvern Mastersizer 2000). The particle sizes were determined before, with and after in-line sonication to investigate the presence of agglomeration. Mass recovery after lyophilisation was also determined.

Results

Figure 3:
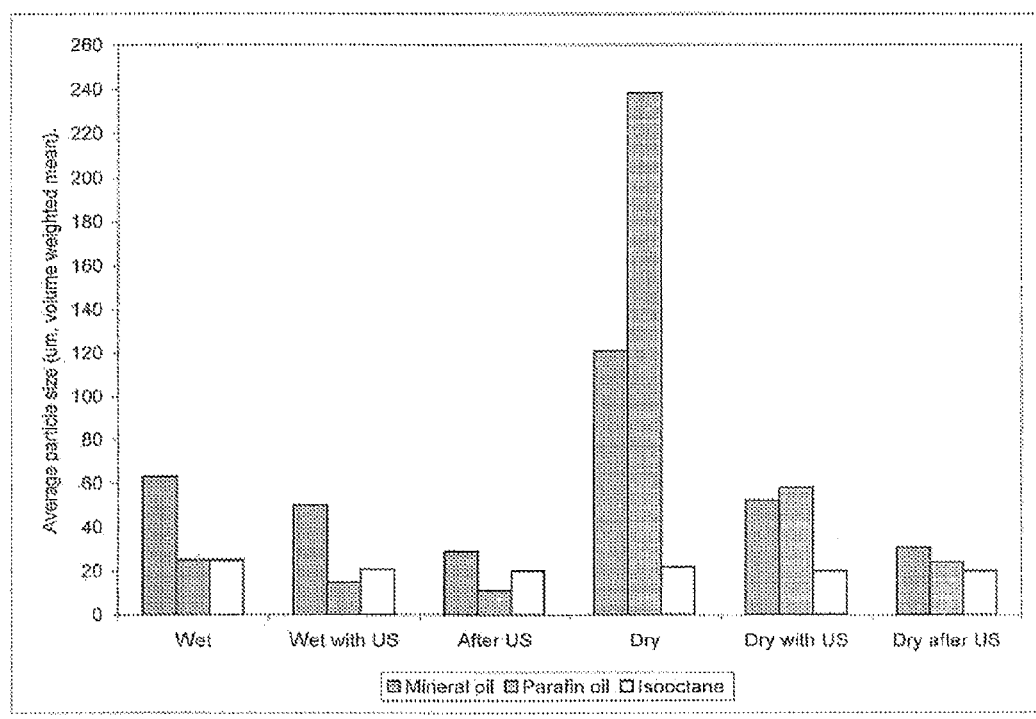
FIG. 3 shows particle size distribution (average size) analyses of particles manufactured using various oil phases, where the particles had not been dried (wet), had been dried (using lyophilisation), with in-line ultrasonication (US) or measured after a pre-treatment with ultrasonication.

Mass recovery of the particles manufactured with different oil phases (20 ml total volume of each) was determined to be 111 mg, 90 mg and 79 mg for mineral oil, paraffin oil and isooctane respectively. Comparison of non-sonicated wet and dry particles manufactured in various oil phases revealed that after drying the average particle size increased for mineral oil and paraffin oil samples (FIG. 3). The particles manufactured in isooctane remained relatively unchanged despite the drying step. In-line sonication and pre-sonication showed large decreases in particle size distribution of dried particles manufactured in mineral and paraffin oils, indicating that after drying the particles were agglomerating (FIG. 3), but could be separated by sonication. Particle size analysis of the wet particles made in mineral and paraffin oils also indicated decreased average particle size with sonication treatment of the particles, although to lesser extent than with dried particles (FIG. 3). Particles manufactured in isooctane remained relatively unchanged irrespective of the drying or sonication treatments.

In conclusion various oil phases can be used to manufacture particles. The use of different oil phases (which presumably influences emulsion droplet size) as well as various post treatment techniques such as drying or sonication can be used to manipulate their size.

Example 4

Manufacture of PEI Support Lattice of Polymeric Strands/Fibres or Network Backbone Using Various Surfactants In the synthesis of the particles the surfactant type may have influence. This was investigated.

The particles were prepared according to Example 3 with the following exceptions—only mineral oil was used as the oil phase and the surfactant type was varied.

Results

Figure 4:
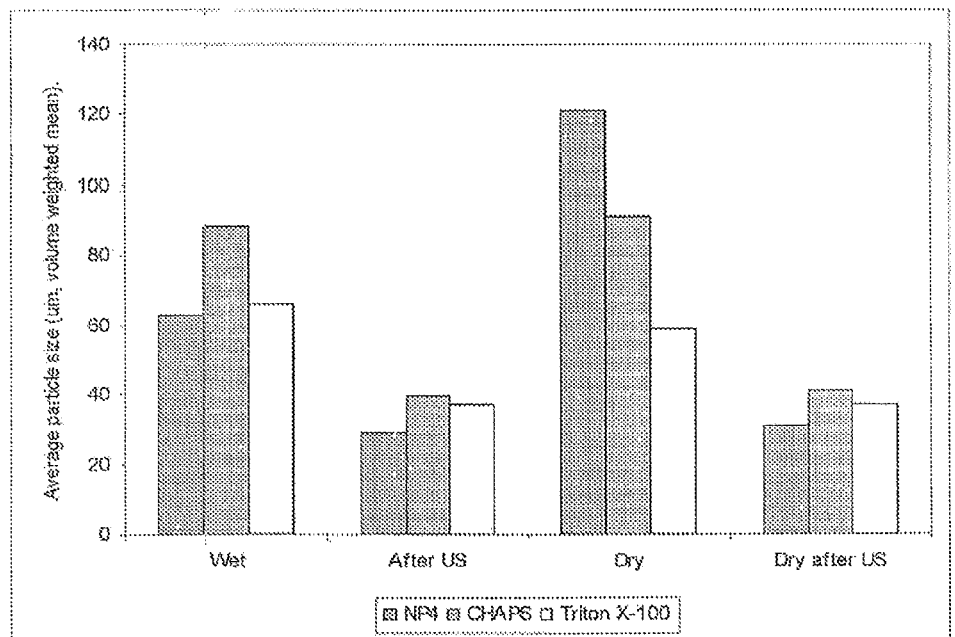
FIG. 4 shows particle size distribution analyses of particles manufactured using various surfactants; determined by light scattering as is, or analysis after ultrasonication (after (US)

Mass recovery of the particles manufactured with various surfactants in mineral oil (20 ml total volume) was determined to be 111 mg, 72 mg and 92 mg for nonoxynol-4, CHAPS and Triton X-100 respectively. Drying of particles manufactured with different surfactants revealed no real size difference when CHAPS and Triton X-100 were used (FIG. 4). The drying of particles manufactured with nonoxynol-4 as the surfactant increased particle size by approximately 50% (FIG. 4). Furthermore size analysis after sonication showed constant decreases in the particle sizes of the particles manufactured with all the surfactants tested. Particle size analyses of particles before and after drying after they had been sonicated were similar.

In conclusion the use of various surfactants to manufacture particles was possible. Moreover particle size could be manipulated with various surfactants and post treatments.

Example 5

Synthesis of Particles with Various Polyaldehydes as Polymer Cross-Linkers

The cross-linker aldehyde used in the synthesis of the particles can be varied. Hence glutaraldehyde, dextran aldehyde, and hexamethylene diisocyanate were compared as cross-linkers.

The method for making particles was as in Example 3, with the following exceptions: in one case the glutaraldehyde was replaced with dextran aldehyde (1 ml of 15 mg/ml). In another it was replaced with 0.5 ml hexamethylene diisocyanate (25% v/v).

To 5 ml of the particle suspension was added 6 ml of 5 mg·ml$^{-1}$ purified *Candida antarctica* lipase B (CALB) in Tris-Cl buffer (0.05 M, pH 8.0), which was stirred gently for 1 hour at 25° C. The suspension was then centrifuged and washed twice with 10 ml buffer at 4° C. The suspension was then centrifuged and the pellet resuspended in 10 ml Tris-Cl buffer. The suspension (10 µl) was assayed using p-nitrophenyl butyrate. For comparison 10 µl of 0.5 mg per ml purified *Candida antarctica* lipase B in Tris-Cl buffer (0.05 M, pH 8.0) was also assayed, using an assay based on hydrolysis of p-nitrophenyl butyrate and its subsequent analysis by spectrophotometry (Table 3).

Lipase Activity Assay

The activity of lipase involved the hydrolysis of a p-nitrophenyl ester (p-nitrophenylbutyrate (PNPB) to p-nitrophenol and butyric acid. The release of p-nitrophenol yields a yellow colour which is measured with a UV/Vis spectrophotometer at 410 nm. Activities were determined in triplicate. The solutions were prepared as follows: solution A contained enzyme substrate dissolved in 8 ml propan-2-ol; while solution B contained 267 mg sodium deoxycholate dissolved in 50 mM Tris-buffer (pH 8.0) followed dissolution of 66.7 mg gum arabic. Kinetic assays were performed at 25° C. using a PowerWave microtitre plate reader (BioTek Instruments) with 240 µl of a 1:10 (A:B) mixture of the above mentioned solutions and 10 µl of the immobilised lipase suspension solutions or free enzyme.

Results

TABLE 3 comparison of particles made with various aldehyde cross-linkers - activity of CALB.

| Cross-linker | Free enzyme (0.5 mg · ml–1) | Glutaraldehyde | Dextran aldehyde | Hexamethylene di-isocyanate |
|---|---|---|---|---|
| Pellet colour | Not applicable | Orange | Yellow | White |
| Lipase activity | U · ml$^{-1}$ | U · ml$^{-1}$ | U · ml$^{-1}$ | U · ml$^{-1}$ |
| Sample 1 | 8.74 | 9.45 | 2.31 | 6.13 |
| Sample 2 | 5.72 | 9.10 | 2.10 | 6.13 |
| Sample 3 | 5.99 | 7.50 | 2.52 | 7.56 |
| Average | 6.81 | 8.68 | 2.31 | 6.61 |

Although this process is not optimised, it demonstrates that the particles can be generated using a range of polyaldehyde compounds.

This material could be recovered on a 0.45 µm filter (Sartorius) and reused, giving an average of 7.05 U·ml$^{-1}$ for the glutaraldehyde particle, or 81% of the original activity over 5 recycles.

A similar experiment was performed using the lipase from *Pseudomonas fluorescens* (PFL). The assay for enzyme activity used the p-nitrophenyl esters of butyric acid (PNPB) and palmitic acid (PNPP) as substrates.

TABLE 4 comparison of particles made with various aldehyde cross-linkers - activity of PFL.

| Aldehyde | Total Activity (U) | |
|---|---|---|
| | PNPB | PNPP |
| Free enzyme | 9.51 | 58.5 |
| Hexa-methylene di-isocyanate | 1.04 | 0.7 |
| Glutaraldehyde | 0.08 | 0 |
| Dextran aldehyde | 0.9 | 2 |

Hence various aldehydes could be used to provide both effective cross-linking for particle formation and functional groups to cross-link proteins to the particles. The selection of cross-linker can influence the activity of the enzyme through degree of enzyme denaturation, or degree of accessibility of the particle to substrates and products. The optimum agent may be selected based on the enzyme and the reaction substrate.

Example 6

Manufacture of Particles Using a Bi-Functional Epoxide Cross-Linker

The cross-linker aldehyde used in the synthesis of the particles can be replaced by other cross-linkers, such as di-epoxides, for example 1,4-butanediol diglycidyl ether. This was added (in lieu of glutaraldehyde) to the cross-linker emulsion (B) as 0.5 ml of a neat, 50%, 25% or 12.5% v/v solution and reacted (as per Example 3) at 40° C. for 2 hours. The particles were recovered from the emulsions by centrifugation (3000×g, Sorvall RT7 benchtop centrifuge) for 10 minutes followed by washing 6 fold with 10 ml volumes of deionised water. After washing the final particles were resuspended to 20 ml in deionised water. Those prepared as above with the 12.5% or 25% v/v epoxide solution were the most uniform in shape while those formed using neat of 50% epoxide were large and diffuse.

The binding of protein was investigated using CALB (as per previous example), which was dialysed overnight and reacted with the epoxide based particles (prepared as above with the 12.5% v/v epoxide solution) for one hour with gentle stirring. Enzyme activity was analysed after recovery and washing of lipase bound particles as described in Example 5. All analyses were performed with PNPB as the substrate Results The use of butanediol diglycidyl ether as a cross-linker resulted in the formation of white particles of approximately 0.1 mm in diameter. The particles were however somewhat irregular in shape, indicating aggregation of particles with cross-linking or subsequent cleaning procedures.

Particles produced with 12.5% v/v epoxide solution were incubated overnight in the presence of the enzyme. These particles yielded an activity of 0.28 U·ml$^{-1}$. This demonstrates that particles can be manufactured using an epoxide cross-linker Example 7

PEI Support Lattice of Polymeric Strands/Fibres or Network Backbone Manufactured in a Single Emulsion The method for formation of the particles can be adjusted according to need. For example the particles may be formed through application of a single emulsion.

The polymer and cross-linker can then be mixed instantaneously in the aqueous phase by means of a dual injection device into a mixing chamber. The simplest version of this device could consist of two syringes that inject into a common line at the same point. This can be injected directly into the oil phase. For example, using 20 ml mineral oil in which 0.2 ml nonoxynol-4 was dissolved for approximately 5 minutes and using magnetic stirring at 500 rpm, such a set-up was evaluated. One syringe contained 0.5 ml PEI (10%) and the other contained 0.5 ml glutaraldehyde (20%, grade II). The syringes were depressed simultaneously directly into the mineral oil. The resultant emulsion was stirred for 1 hour and then the particles were recovered as in example 3. The experiment was performed in triplicate. The particles were divided into 2 equal fractions, one of which was freeze dried (Virtis) and re-suspended to original volume before being analysed for particle size distribution (Malvern Mastersizer 2000). The samples were analysed for mass recovery after drying.

Results

The mass recovery for particles manufactured using a single emulsion was calculated to be 152±12 mg, which was approximately 1.4 fold higher than that obtained using the 2 emulsion strategy (Refer to Example 3).

Figure 5:
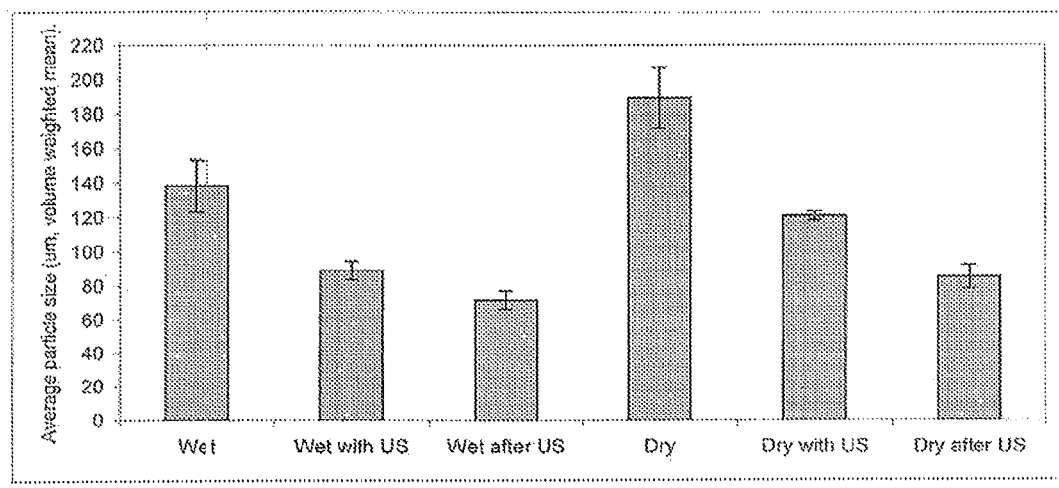
FIG. 5 shows particle size distribution for wet and dry particles manufactured using a single emulsion; results show the standard deviation of triplicate experiments; determined by light scattering as is, with in-line ultrasonication (with US), or analysis after sample pre-ultrasonication (after US)

The formation of particles using a single emulsion was possible and reproducible using the current manufacturing technique (FIG. 5). The particles were found to be larger in particle size distribution than those formed using a dual emulsion (FIG. 5). The size distribution wet and dry obtained for single emulsion particles were shown to be between 50 and 70% larger in size than those obtained for the dual emulsion experiment (FIG. 3).

Example 8

Scaled Manufacture of PEI Support Network or Lattice of Polymeric Strands/Fibres The objective was to linearly increase the scale of particles manufacture 10 fold and evaluate the particle size. Two separate batches of particles were prepared according to the standard manufacturing method outlined in Example 3, except that the second batch contained 10 fold more of each of the respective constituents required. The batches were processed for particle recovery as in Example 3 according to scale.

Results

Figure 6:
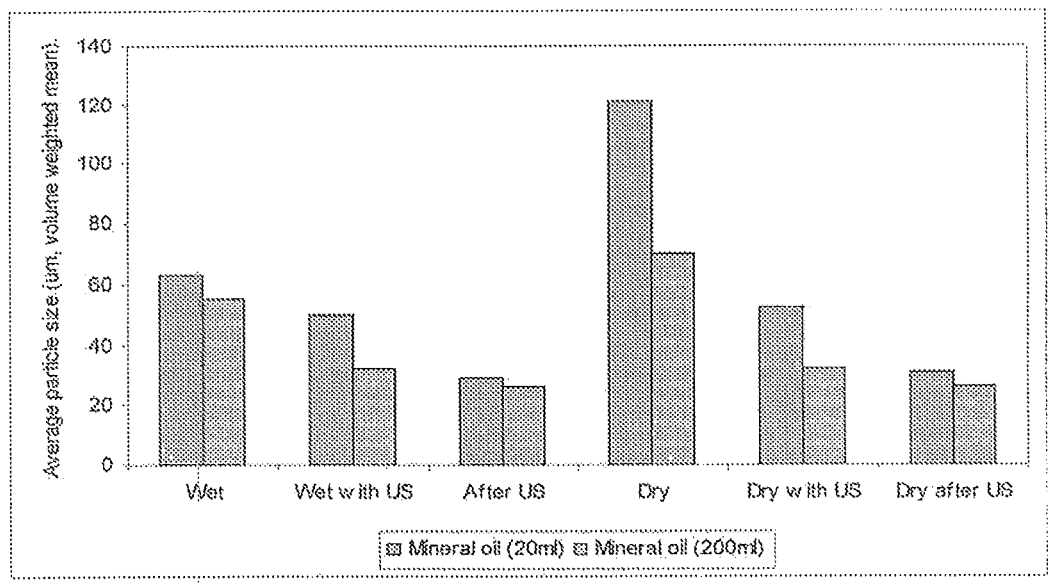
FIG. 6 shows particle size distribution for wet and dry particles manufactured at 20 ml mineral oil volume and 200 ml mineral oil volume.

The mass recovery for particles manufactured at 20 ml and 200 ml mineral oil volumes were calculated to be 0.111 g and 1.11 g respectively which was exactly 10 fold difference. The manufacture of particles at mineral oil volumes of 20 and 200 ml was possible with the larger scale manufactured particles being consistently only slightly smaller in particle size than those obtained at 20 ml scale (FIG. 6). Interestingly the non-sonicated dried particles manufactured at larger scale were around 50% smaller in size when compared to the dried particles at the smaller scale (FIG. 6).

The manufacture of particles under standard conditions is scalable by at least 10 fold based on mass recovery and particle size analysis.

Example 9

Application of a PEI Support Network or Lattice of Polymeric Strands/Fibres to Immobilise a Range of Enzyme Classes The objective was to bind different enzymes to the particles backbone and calculate their binding percentages as well as the enzymatic activity retained.

The particles manufactured according to example 3 were used. The enzymes investigated were Laccase (Novozymes 51009, *Myceliopthora thermophilia*), Glucose oxidase (Seravac Pty Ltd, *Aspergillus niger*) and Lipase (CALB, Novozymes *Candida antarctica*). For each experiment 5 mg (0.5 ml at 10 mg·ml$^{-1}$) of the respective enzyme was bound to 14 mg (0.5 ml at 28 mg·ml$^{-1}$) of particles with gentle shaking for 2 hours (25° C.). Each sample was centrifuged for 10 minutes using an Allegra X22R centrifuge (2000×g). The particles were washed 6 times consecutively, each time with 2 ml deionised water. The combined supernatant fractions were analysed for total protein. Each of the respective enzyme binding experiments was performed with and without the inclusion of a particular substrate as a potential protectant. For laccase the commercial mediator Denillite II Assist (Novozymes) was the potential protectant (50 µl of 100 mg·ml$^{-1}$ pH adjusted to 6.8), for glucose oxidase the potential protectant was glucose (50 µl of 10% m/v glucose monohydrate) and for CALB an 8 diasterioisomeric mix of 2-isopropyl-5-methylcyclohexanol (menthol) was used (50 µl). The particles were resuspended to 2 ml in deionised water. Particles were assayed for their respective enzyme activities. All assays were in triplicate.

Total Protein

Total protein assays were performed using the Bio-Rad Total Protein Assay kit (Cat. No.: 500-0006) with each of the respective enzymes used as standards.

Laccase activity was determined by using 1 mM 2,2_-Azino-bis(3-ethylbenzothiazoline-6-sulfonic acid) diammonium salt (ABTS) as the substrate in 100 mM succinate-lactate buffer pH 4.5. The optical density of the solution was measured at 420 nm. These assays were performed by adding 20 µl of the samples to 180 µl of ABTS reagent. Activity was followed spectrophotometrically at 420 nm using a PowerWave HT (Biotek Instruments) with incubation at 25° C.

Glucose Oxidase

Glucose Oxidase (GOX) activity was measured using the indirect oxidation of o-dianisidine by horseradish peroxidase (HRP). The assays were performed according to Bergmeyer et al., 1988. The following reagents were prepared: reagent A, 0.1 M potassium phosphate buffer, pH 7, containing o-dianisidine.2HCl (0.006%); reagent B, 10% aqueous solution of D-glucose (allowed to mutarotate for 1 h before use); reagent C, 60 Uml$^{-1}$ HRP aqueous solution. Reagents A, B and C were mixed immediately prior to assaying for glucose oxidase in the ratio 24:5:1, respectively. The reaction contained 0.3 ml of the reaction reagent and was initiated by the addition of 10 µl of sample. The reaction was measured kinetically at 436 nm (Powerwave HT microtiterplate reader) at 25° C. One unit of glucose oxidase activity is defined as the amount of enzyme that catalyses the conversion of 1 µmole β-D-glucose to D-gluconolactone and H$_2$O$_2$ per minute at 25° C. and pH 7.

Lipase

The activity of lipase involved the hydrolysis of p-nitrophenyl esters to p-nitrophenol and an aliphatic carboxylic acid. The release of p-nitrophenol yields a yellow colour which is measured with a UV/Vis spectrophotometer at 410 nm. Two p-nitrophenol esters were used, p-nitrophenylacetate (PNPA) and p-nitrophenylbutyrate (PNPB) and activities were determined in triplicate. The solutions were prepared as follows: solution A contained enzyme substrate (11.6 mg PNPA or 24 mg PNPP) dissolved in 8 ml propan-2-ol; while solution B contained 267 mg sodium deoxycholate dissolved in 50 mM Tris-buffer (pH 8.0) followed by 66.7 mg gum arabic. Kinetic assays were performed at 25° C. using a PowerWave microtitre plate reader (BioTek) with 240 µl of a mixture of the above mentioned solutions and 10 µl of the spherezymes or free lipase solutions.

Results

The protein loading for all the enzymes tested for binding to particles ranged between 30% to 36% (Table 5).

TABLE 5

Binding efficiency of various enzymes to particles backbone support

| Sample | Particles Dry Weight (mg) | Bound Protein (mg) | Protein loading (mg · g-1) | Protein Loading (% m/m) |
|---|---|---|---|---|
| Laccase | 14 | 4.77 | 341 | 34.06 |
| Laccase - Substrate* | 14 | 5 | 357 | 35.71 |
| Glucose Oxidase | 14 | 5 | 357 | 35.71 |
| Glucose oxidase-Substrate* | 14 | 5 | 357 | 35.71 |
| CALB | 14 | 4.27 | 305 | 30.5 |
| CALB -Substrate* | 14 | 4.6 | 329 | 32.89 |

*Substrate was added during enzyme immobilisation in order to protect active site (refer to method above)

Figure 7:
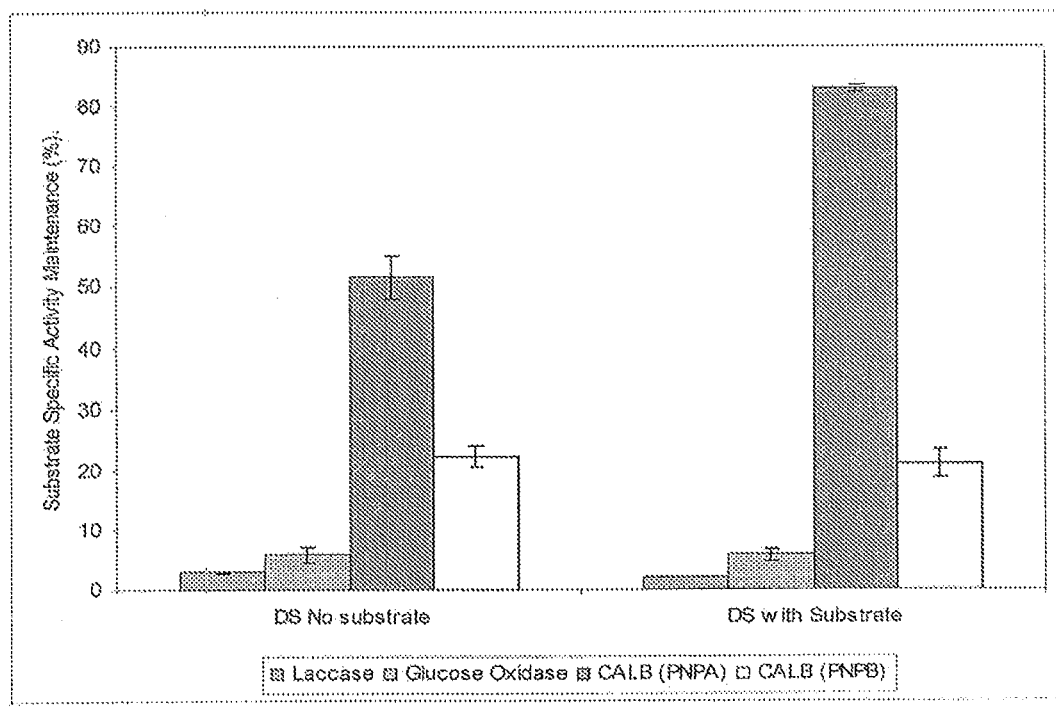
FIG. 7 shows activity maintenance of various enzymes bound to particles, with and without substrates as potential protectants.

The inclusion of the menthol substrate for activity maintenance of CALB towards PNPA was advantageous retaining approximately 30% more activity (83%) (FIG. 7).

Laccase, glucose oxidase and CALB were all successfully bound to particles with retention of activity, indicating that a range of proteins can be effectively bound to the particles at high protein loading. Furthermore, other enzymes, such as horseradish peroxidise, protease and dehydrogenases, were also demonstrated to bind to the particles (see examples below).

Example 10

PEI Support Network or Lattice of Polymeric Strands/Fibres; Particles with Multiple Enzymes Bound The investigation was designed to demonstrate that more than 1 enzyme could be bound to the particles backbone with retention of activity towards both enzymes. The glucose oxidase and horseradish peroxidase system was chosen.

The particles were manufactured according to Example 3. The enzymes investigated were glucose oxidase (Seravac Pty Ltd, *Aspergillus niger*) and horseradish peroxidase (Serevac Pty Ltd). For the example 5 mg (0.5 ml at 10 mg·ml$^{-1}$) glucose oxidase and 10 mg of horseradish peroxidase (1 ml at 10 mg·ml$^{-1}$) was bound to 28 mg (1 ml at 28 mg·ml$^{-1}$) of particles backbone with gentle shaking for 2 hours (25° C.). Each sample was centrifuged for 10 minutes using an Allegra X22 centrifuge (200×g). The particles were washed 6 times consecutively each with 2 ml deionised water. The combined supernatant fractions were analysed for total protein. The activity of the particles was determined according to the assay method for glucose oxidase in Example 9, but without the inclusion of horseradish peroxidase in the assay reagent.

Results

Glucose oxidase and horseradish peroxidase were successfully bound to particles backbone and able to convert glucose at a rate of 3 μmole·min$^{-1}$ (Table 6). As the assay detected activity, this indicates that both glucose oxidase and horseradish peroxidase were bound and active. Hence particles can be used to bind more than one enzyme and where both enzymes retain activity.

TABLE 6

Binding efficiency and activity for the glucose oxidase and horseradish peroxidase dual enzyme particles.

| Sample | Particles Dry Weight (mg) | Bound Protein (mg) | Protein Loading (mg · g$^{-1}$) | Protein Loading (% m/m) | Glucose Oxidase Activity (μmole · min$^{-1}$) |
|---|---|---|---|---|---|
| Glucose Oxidase and horseradish peroxidase | 28 | 6.7 | 240.7 | 24.1 | 3 |

Example 11

PEI Support Network or Lattice of Polymeric Strands/Fibres Manufactured Using Various Drying Methods The aim was to manufacture particles and subsequently dry them using different methods, such as lyophilisation, vacuum and acetone drying.

The particles were manufactured under the standard conditions as outlined in Example 1. Once washed, the particles were dried by lyophilisation (Virtis Genesis freeze drier), vacuum drying using a vacuum cconcentrator (Savant SpeedVac SC110, fitted with a Savant RVT100 vapour trap), or by dehydrating with acetone followed by air drying at 25° C. for 12 hours. The acetone dried particles could not be re-suspended in aqueous medium due to agglomeration, and hence were not considered further.

However, vacuum drying and lyophilisation were both successful techniques for drying the particles and could subsequently be used for the attachment of a range of enzymes or proteins (Table 7). To 5 ml of the particle suspension was added 6 ml of 5 mg per ml purified enzyme in Tris-Cl buffer (0.05 M, pH 8.0), which was stirred gently for 1 hour at 25° C. The suspension was then centrifuged and washed twice with 10 ml buffer at 4° C. The suspension was then centrifuged and the pellet resuspended in 10 ml Tris-Cl buffer (0.05 M, pH 8.0). The particle sizes were determined using a Malvern Mastersizer.

Results

TABLE 7

Average particle size after various drying treatments.

| Sample | Drying Method | Treatment | Particle size μm (volume weight mean) Wet particles | Particle size μm (volume weight mean) Re-Suspended Dried Particles |
|---|---|---|---|---|
| Particles - No immobilised protein | Lyophilisation | None | 22.432 | 17.662 |
|  |  | Sonication | 13.141 | 14.556 |
| Particles - CALB | Lyophilisation | None | 21.958 | 26.262 |
|  |  | Sonication | 14.199 | 13.734 |
| Particles - BSA | Lyophilisation | None | 24.114 | 32.092 |
|  |  | Sonication | 20.071 | 21.129 |
| Particles - Pseudomonas fluorescens lipase | Lyophilisation | None | 18.705 | 21.648 |
|  |  | Sonication | 14.169 | 15.258 |
| Particles - No immobilised protein | Vacuum drying | None | 17.662 | 66.613 |
|  |  | Sonication | 14.556 | 18.979 |
| Particles - Pseudomonas fluorescens lipase | Vacuum drying | None | 18.705 | 71.776 |
|  |  | Sonication | 14.169 | 18.84 |
| Particles - Laccase | Lyophilisation | None | 38.081 | 34.491 |
|  |  | Sonication | 22.498 | 18.948 |
| Particles - Alcalase Protease (Novozymes) | Lyophilisation | None | 30.737 | 32.884 |
|  |  | Sonication | 20.297 | 22.698 |

This example demonstrates that with drying, particularly with lyophilisation, particles with bound enzyme do not agglomerate to any great extent.

Example 12

Characterisation of Laccase Binding to Support Network of or Lattice of Polymeric Strands/Fibres Prepared from PEI at Various pH's The effect of drying on the properties of laccase after binding bound particles on the enzymes characteristics was determined.

Particles were manufactured according to the standard method of manufacture outlined in Example 3 except that in addition to the pH 11 preparation of the PEI (10%) a preparation adjusted to pH 8 was also evaluated. Thereafter laccase was immobilised to the backbone as described in Example 9 with the following exceptions: 1 ml of laccase (Novozyme 51004, 50 mg·ml$^{-1}$) was reacted with 6.25 ml particles (16 mg·ml$^{-1}$), therefore 50 mg of laccase was bound per 100 mg of particles. The laccase bound particles were washed with 12.5 ml deionised water and resuspended to 20 ml using deionised water. The particles were divided into 2 equal fractions of 10 ml each, of which a sample was freeze dried for mass recovery determination, and to investigate the characteristics of both wet and dry laccase bound particles. The dried samples were resuspended to their original volumes with deionised water. All assays were in triplicate.

Total protein of the laccase supernatant samples was determined using the Bio-Rad Total Protein Assay kit (Cat. No.: 500-0006) with laccase as the protein standard. Laccase activity was determined according to Example 9.

Results

Drying of laccase bound particles by lyophilisation showed that higher mass recovery was achieved when particles were manufactured with PEI at pH 11 (Table 8), although more laccase protein was bound to the particles using PEI at pH 8 for manufacture. Optimum activity maintenance towards ABTS was achieved with non-lyophilised particles manufactured using pH 8 PEI (16%), but after lyophilisation the same sample only retained 3% of the laccase activity. It was noted that particles manufactured using pH 8 PEI were difficult to re-suspend after drying, and therefore probably agglomerate, thereby reducing surface to area ratio, and hence reducing activity due to diffusional constraints on the substrate and product. The same effect on activity was not observed for particles generated using PEI at pH 11 (Table 8).

TABLE 8

Binding efficiency and activity maintenance of laccase bound particles manufacture at various PEI pH values with and without freeze drying.

| Laccase particle preparation conditions | Particles Dry Weight (mg) | Protein (mg) | Protein Loading (mg · g$^{-1}$) | Protein Loading (%) | Laccase Activity Maintained (%) |
|---|---|---|---|---|---|
| particles wet pH 8 | NA | 25 | 383 | 38 | 16 |
| particles dry pH 8 | 65 | 25 | 383 | 38 | 3 |
| particles wet pH 11 | NA | 25 | 295 | 30 | 8 |
| particles dry pH 11 | 83 | 25 | 295 | 30 | 11 |

This experiment demonstrates that particles can be prepared with PEI of varying pH's and that this changes the binding properties of the particles for enzymes.

Example 13

Figure 8A:
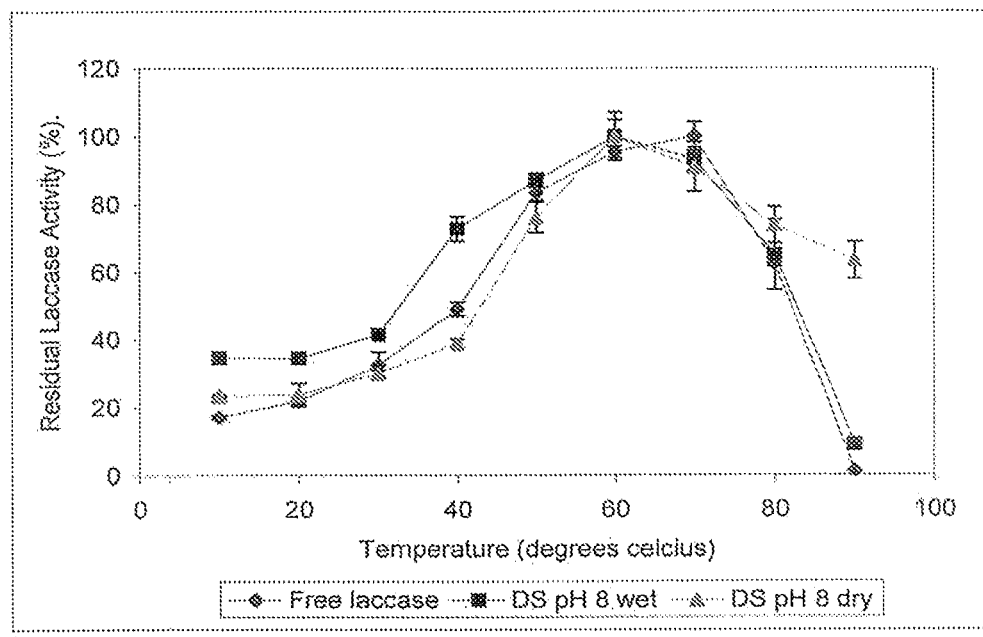
FIG. 8 shows temperature optima for free laccase and wet and dry laccase bound particles manufactured at PEI pH of 8 (FIG. 8A) and 11 (FIG. 8B)
Figure 8B:
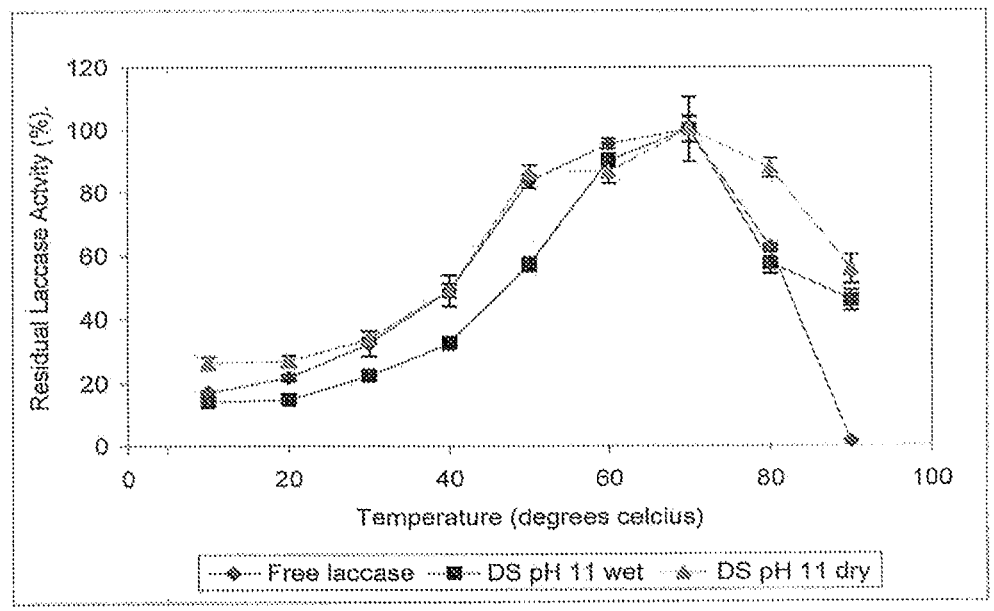
Figure 9:
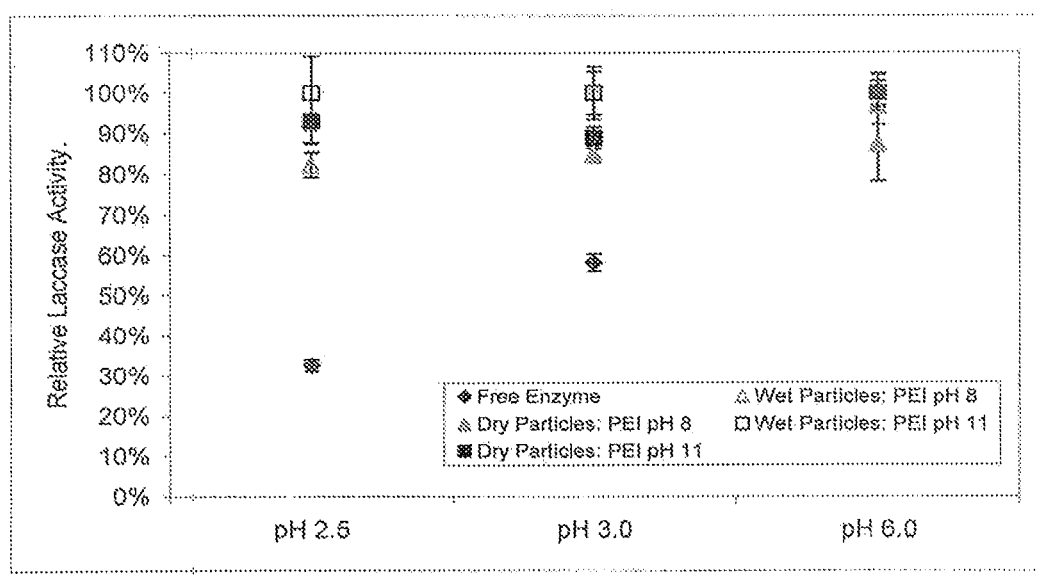
FIG. 9 shows pH stability (6 hours) for free laccase and wet and dry laccase bound particles manufactured at PEI pH's of 8 and 11.
Figure 10A:
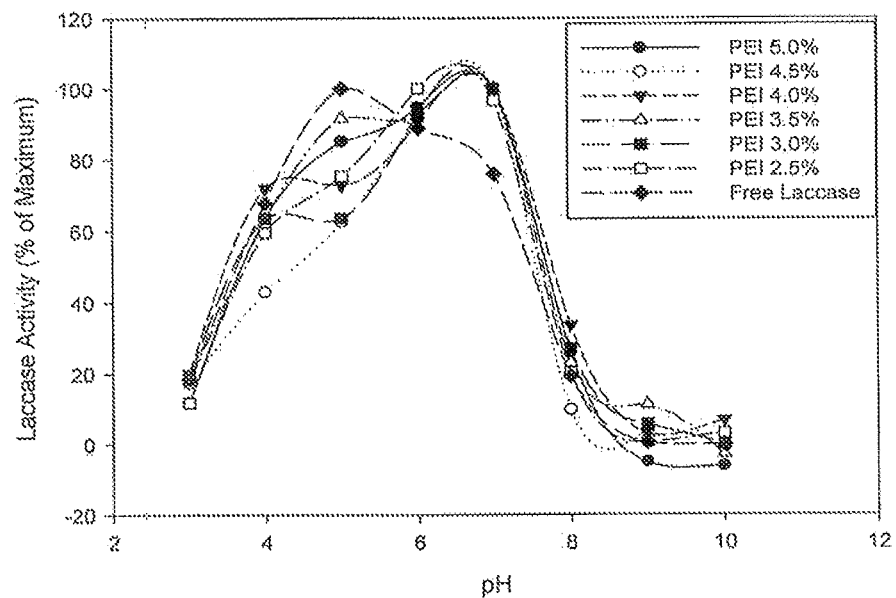
FIG. 10A shows laccase pH profiles of immobilised and free enzymes on non-post-treated fibrous lattices or networks, in accordance with Example 14, indicating the effect of varying polyethyleneimine ('PEI') concentration on pH profile shifting.
Figure 10B:
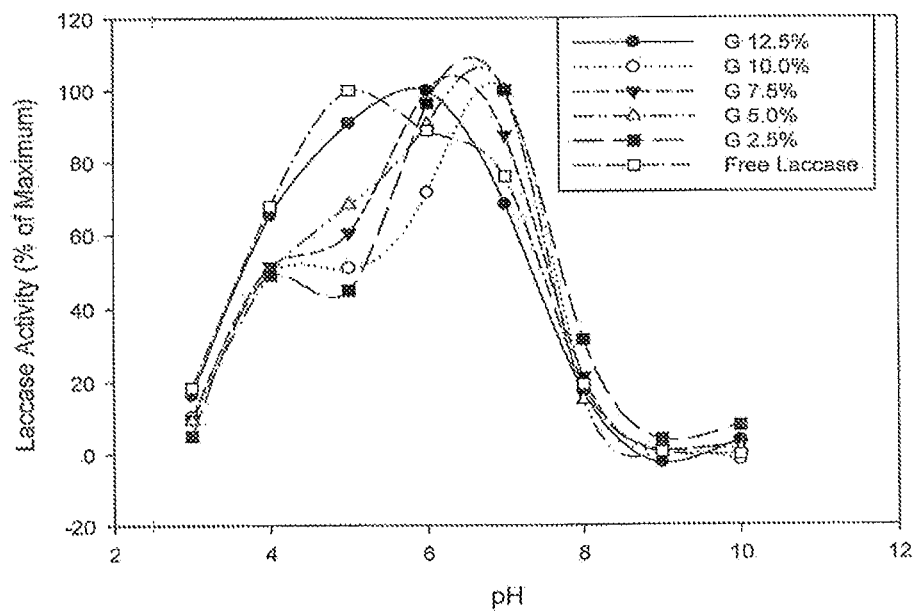
FIG. 10B shows laccase pH profiles of immobilised and free enzymes on non-post-treated fibrous lattices or networks, in accordance with Example 14, indicating the effect of varying or glutaraldehyde concentration on pH profile shifting.
Figure 11A:
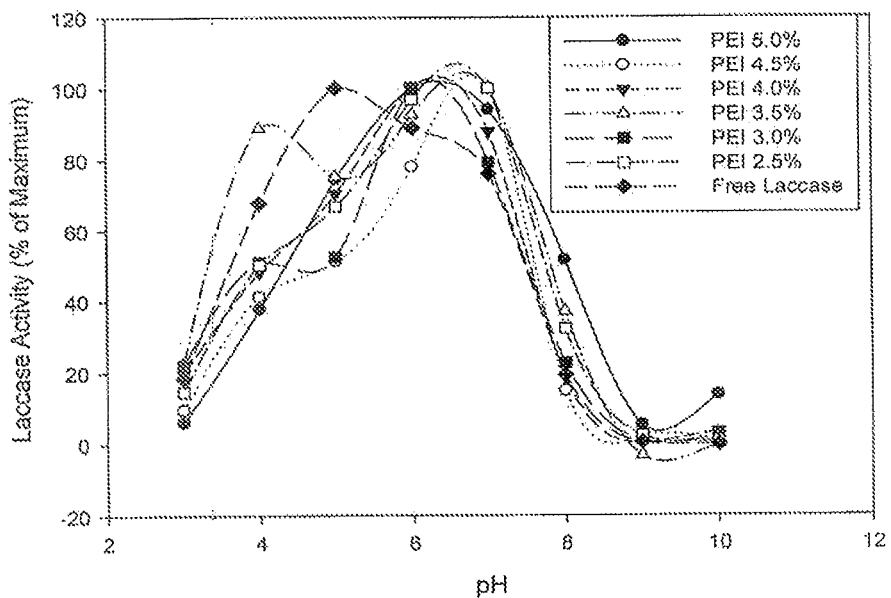
FIG. 11A shows laccase pH profiles of immobilised and free enzymes on glutaraldehyde post-treated fibrous lattices or networks, in accordance with Example 14, indicating the effect of varying PEI concentration on pH profile shifting.
Figure 11B:
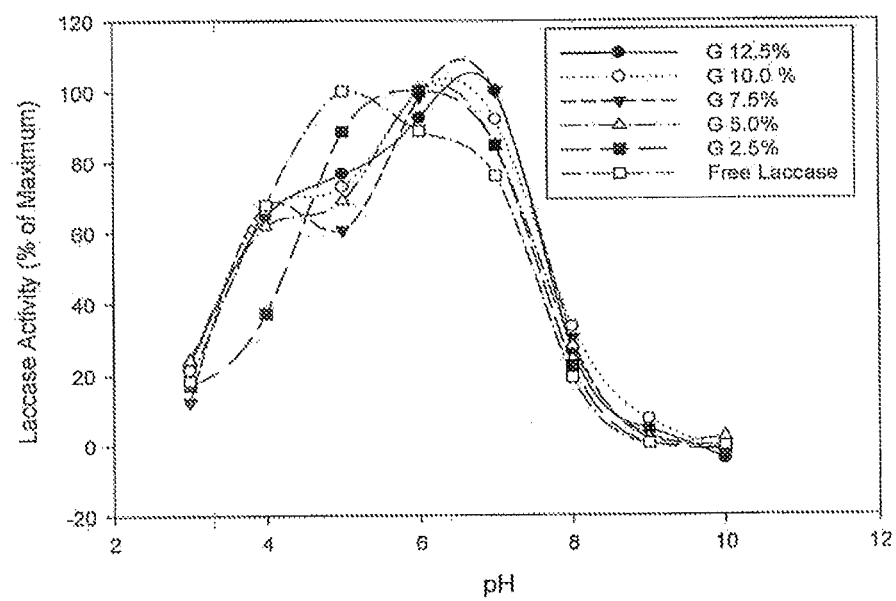
FIG. 11B shows laccase pH profiles of immobilised and free enzymes on glutaraldehyde post-treated fibrous lattices or networks, in accordance with Example 14, indicating the effect of varying the glutaraldehyde concentration on pH profile shifting.

Stability of Laccase Bound to PEI Support Network or Lattice of Polymeric Strands/Fibres Manufactured at pH 8 or 11 and Lyophilised The thermostability and pH stability of laccase bound to PEI support network or lattice of polymeric strands/fibres manufactured at pH 8 and 11 and lyophilised was determined (laccase bound particles produced as described in Example 12).
Temperature Optima
The temperature optima profiles of free laccase and laccase bound particles (at equivalent protein loading) was performed using 1 mM ABTS as the substrate in 100 mM succinate-lactate buffer (pH 4.5). Samples (100 μl) were added to 1.9 ml of substrate pre-equilibrated to the correct temperature in a water bath. Assays were performed using a DU800 spectrophotometer (Beckman-Coulter, 420 nm) fitted with Peltier temperature controller. The spectrophotometer was set to the temperature of interest and cuvettes were allowed to equilibrate for 5 minutes prior to addition of reagent equilibrated in a water bath.
pH Stability
The pH stability of free laccase and laccase bound particles (at equivalent protein loading) was done with ABTS (1 mM) in 100 mM succinate-lactate buffer (pH 4.5). The respective laccase samples were incubated in the Britton-Robinson universal buffer at pH 2.5, 3 and 6. Samples (20 μl) were periodically removed and assayed (230 μl assay reagent) at 420 nm using a PowerWave HT (Biotek Instruments) with incubation at 25° C. The 6 hour time points for this experiment are illustrated in FIG. 9 below.
Results
The results are shown in FIGS. 8A, 8B and 9.
Both the laccase bound to particles and the free (non-immobilised) laccase were optimally active at 70° C. (FIG. 8). However, laccase bound to particles indicated improved thermostability at 90° C. (55-65% activity) in comparison to the free laccase (0% activity) in the time taken to prepare samples for assay. There was also a minor improvement when the dried particles were used, suggesting that with drying there is an advantage. This may be due to more protein-particle links being formed as water is removed. This in turn would increase the multi-point covalent binding of the protein or enzyme, which is known to provide greater stability, such as improved thermostability [Improvement of enzyme activity, stability and selectivity via immobilization techniques. Mateo, C., Palomo, J. M., Fernandez-Lorente, G., Guisan, J. M., Fernandez-Lafuente, R. 2007 Enzyme and Microbial Technology 40 (6), pp. 1451-1463].

The pH stability of laccase bound particles and free enzyme at pH 2.5, 3 and 6 was also determined. At pH 2.5 and pH 3 all the laccase bound particle samples retained 80-110% activity while the free enzyme had lost approximately 70 and 40% activity respectively (FIG. 9). Hence the immobilisation provides improved pH stability. All the samples including the free enzyme were stable at pH 6 after 6 hours.

Hence, the immobilisation of enzymes on particles of PEI support network or lattice of polymeric strands/fibres can provide additional stability in extremes of pH.

Example 14

Enzyme pH Optimum Shift with Immobilisation to PEI Support Network or Lattice of Polymeric Strands/Fibres Enzymes have an optimum pH for activity. In some cases the optimum pH of an enzyme does not coincide with the optimum pH for other aspects of a reaction. For example the enzyme substrate/reactant may be optimally soluble at another pH. Another example is where more than one enzyme is used in a multi-step one-pot reaction, and their pH optima may not coincide. Hence, should an enzyme optimal pH change during immobilisation, this could provide commercial and technical advantages. Hence the pH optimum of a laccase was determined with and without immobilisation on the particles.
Enzyme Assays
Laccase reagent contained 1 mM guaiacol in 50 mM Britton-Robinson universal buffer (Davies T J, Banks C E, Nuthakki B, Rusling J F, France R R, Wadhawana J D, Compton R G. 2002. Surfactant-free emulsion electrosynthesis via power ultrasound: electrocatalytic formation of carbon-carbon bonds. Green Chem. 4:570-577) adjusted to the pH values of interest. The universal buffer was used to ensure that the same buffer system was present and could effectively buffer across a wide pH range. Assays were performed in triplicate at 450 nm with an extinction coefficient of 5 200 M$^{-1}$·cm$^{-1}$. pH Profiles of laccase immobilised to the particles of support network or lattice as well as the free enzyme were experimentally determined. Assays were performed using a PowerWave HT Microtitre plate reader. One unit of enzyme was defined as the quantity of enzyme required to oxidise 1 μmol of substrate per minute.
pH Profile Shifting
pH profiles were determined for laccase bound to the fibrous lattice or network backbone support since pH profile shifting has been known to occur during immobilisation. Particles were made as per Example 3. The effect of varying glutaraldehyde and PEI concentration on the pH optimum shift was also investigated as was the effect of gluraldehyde post-treatment (Example 2, A2-J2).

Results

The results are shown in FIGS. 10A, 10B, 11A and 11B.

The general trend with respect to pH profile shifting is towards a neutral to slightly alkaline pH. This example demonstrates that the pH profile of enzymes may be shifted by immobilisation to the particles.

Example 15

Various Functionalities of PEI Network or Support Lattice of Polymeric Strands/Fibres The functionality of the particles backbone can be changed to demonstrate hydrophobic, ionic and affinity based binding of proteins.

The particles were manufactured by mixing an emulsion of 10 ml of mineral oil containing 0.1 ml nonoxynol-4 and 0.5 ml polyethyleimine solution, pH 11, and an emulsion of 10 ml of mineral oil containing 0.1 ml nonoxynol-4 and 0.5 ml glutaraldehyde (Sigma grade II). Both emulsions had been agitated at 500 rpm for 30 min prior to mixing. The combined emulsion was agitated at 500 rpm for 30 min. This provided unmodified particles which were recovered by centrifugation as described previously.

Ionic Binding

Ionic groups were generated on above unmodified particles by functionalisation with glutaraldehyde (200 µl of 25% aqueous solution—washed with 3×20 ml of deionised water) followed by treatment with ethylene diamine (1 ml of 0.33 M) to react with free aldehyde residues (1 hour at room temperature with periodic inversion). Particles were washed repeatedly with excess dionised water and recovered by centrifugation at 2000×g for 10 minutes. Laccase (2.5 mg) was incubated with 5 mg of modified particles for 30 minutes at 4° C. with periodic inversion to ensure adequate mixing. To determine ionic binding 1.0M NaCl (as a counter-ion) was added to the laccase bound particles and mixed by inversion for 5 minutes. Particles were recovered by centrifugation (as mentioned above) and activity determined.

Hydrophobic Binding

Hydrophobic groups were added to the particles by incubating the unmodified particles (5 mg) with epoxyoctane (0.1 ml) at 25° C. for 4 hours. These were then repeatedly washed with excess water and recovered by centrifugation (as mentioned above). Hydrophobically bound protein (*Pseudomonas fluorescens* lipase, 5 mg) could be removed by addition of a surfactant (1% deoxycholate), as determined by measuring protein absorbance at 280 nm.

Affinity Binding

Affinity binding of proteins is demonstrated in Example 17.

Results

Ionic Binding

45% of the added laccase was bound to the modified particles (as determined by the Bio-Rad protein assay dye reagent method, 500-0006, as per the manufacturers protocol). Of this 45%, 76.9% of the laccase could be removed through addition of salts (1.0 M NaCl) as a counter-ion. In comparison unmodified particles only bound 14% of the laccase, and only 52.6% of this could be removed by the salt solution.

Hydrophobic Binding

Protein was bound to the modified particles. Approximately 28% of the protein bound by the modified particles was removed by the addition of deoxycholate, this being the hydrophobically bound portion of the bound enzyme.

This example demonstrates that the functionality of the particle matrix can be modified to effect alternative mechanisms of protein binding to the particle matrix.

Example 16

Co-Entrapment of Mediators and Co-Factors

Inclusion of co-factor (or modified co-factor, or mediator) permits co-entrapment of the co-factor with the enzyme after cross-linking. Through selection of process conditions, the porosity of the particle can be arranged to retain the co-factor while permitting entry and exit of small molecules, such as reactants, e.g. enzyme substrates, co-substrates, products and co-products.

Amino acid dehydrogenase (AADH), formate dehydrogenase (lyophilised) were purchased from Biocatalytics (USA). PEG 20000-NADH was obtained from Jülich Fine Chemicals (Germany). Mineral oil was obtained from Castrol (Germany). Nonoxynol-4 was obtained from ICI (UK). Glutaraldehyde (Glut) (25% aqueous solution) was obtained from Acros Organics (Belgium). Formic Acid was obtained from Merck (Germany). Ethylenediamine (EDA), Polyethyleneimine (PEI), 3-Methyl-2-oxobutyric acid (2-Ketovaline), DL-valine, NADH and $NAD^+$ were obtained from Sigma-Aldrich.

Polymeric particles were produced by cross-linking polyethyleneimine (PEI) with glutaraldehyde. A water-in-oil emulsion of the polyethyleneimine was prepared by emulsifying 800 µl of 10% PEI in 40 ml of mineral oil containing 200 µl of pre-dissolved Nonoxynol-4 (20 minutes magnetic stirring in 100 ml beaker with a 20 mm magnetic stirrer stirring at 500 rpm). A second water-in-oil emulsion was prepared similarly using a 20% glutaraldehyde solution. The two emulsions were mixed by adding the glutaraldehyde emulsion to a rapidly stirring polyethyleneimine emulsion (700 rpm). This was allowed to react for 30 minutes with continuous stirring.

The polymeric particles were recovered by centrifugation at 2000×g for 10 minutes (Sorvall, RT7). The polymer particles were washed 4 times with 45 ml of deionised water. Recovery during washing was performed by centrifugation as in previous examples. The product was re-suspended to a volume of 10 ml. This solution (1 ml) was aliquoted into eppendorf tubes and used in subsequent experiments.

Protein solutions of each protein (formate dehydrogenase and valine dehydrogenase) containing 10 mg·ml$^{-1}$ were prepared. These two solutions were subsequently mixed (200 µl of each solution) and incubated with the polymeric material. This solution was mixed by inversion and allowed to react for 30 min with gentle agitation. The particles containing immobilised enzyme were assayed for activity determination using the methods described below.

The particles were washed with deionised water, and recovered as mentioned above. The particles were mixed with 100 µl PEG20000-NADH (obtained from Jülich Fine Chemicals of Mich, Germany) and incubated at room temperature with gentle agitation for 2 hours. This solution was subsequently lyophilised. The lyophilised product was washed twice with 2 ml of water and recovered by centrifugation. The particles were re-suspended in 1 ml of 100 mM Tris-Cl buffer pH 8.0 containing 100 mg of lysine to quench excess aldehyde functionality on the particles, and incubated at room temperature for 1 hour. The particles were washed 5 times with 2 ml of Tris-Cl buffer (20 mM pH 8.0). This sample was then tested for recycling ability using 1 ml of the recycling reagent. The samples were washed 3 times with 2 ml volumes of water between each cycle. Samples were analyzed for the production of valine by amino acid TLC and HPLC as mentioned below.

These particles were reacted and recycled into fresh reaction medium for subsequent reactions.

Recycling Reagent

Reagent for the recycling of PEG-20000-NADH for the production of valine consisted of 50 mM formate (from 1 M stock of sodium formate pH 8.0), 50 mM Tris-Cl buffer pH 8.0, 50 mM ammonium tartrate, and 10 mM 2-ketovaline. The composition of this reagent was formulated to ensure that valine was only produced if the PEG NADH was recycled.

Analytical Methods

Amino acid TLC was performed on F254 silica gel plates (Merck). The mobile phase used was 9:1 ethanol to glacial acetic acid. The amino acid (valine) was stained using a solution of 2% ninhydrin in acetone. The plates were heated at 120° C. until suitable resolution of valine (Rf 0.49) and ammonia (Rf 0.31) was clearly visible.

HPLC was performed using the OPA derivitisation method (o-phthalaldehyde reagent) for determination of amino acids. Samples were derivatised in-line. Valine standards were included.

Results

The reaction and recycle was a success according to TLC data, with formation of valine spots for all of the consecutive particle catalysed reactions. Positive TLC results were confirmed and quantified using the HPLC OPA method, with the particles converting 48, 35, 59, 43, 33, and 29% of 10 mM ketovaline to valine respectively in six consecutive 16 hour reaction cycles This example demonstrates the entrapment of co-factors in the enzyme-particle matrix allowing enzymes that use co-factors to maintain functionality and allowing re-cycling of entrapped co-factors.

Example 17

Binding of Antibodies by Particles of PEI Support Network or Lattice of Polymeric Strands/Fibres This example demonstrates the binding of antibody and/or antigen on the particles. The binding of antibodies and antigens demonstrates the suitability of the particles for affinity binding of proteins via immobilised antibody or antigen. Further, the plausibility of the particles for diagnostic applications, such as ELISA, is demonstrated.

Polyethyleneimine (P3143; 50% aqueous solution), glutaraldehyde grade II (G6257; 25% aqueous solution), mineral oil (M8410), the antigen mouse interleukin 2 (10523-20UG; SL06092) and the marker enzyme streptavidin-peroxidase from *Streptomyces avidinii* (S5512-250UG; SL05181) were from Sigma-Aldrich. The primary antibody, rat anti-mouse interleukin 2 (IL-2) MAB (I7663-27K1; L6080801) and the secondary antibody, rat anti-mouse interleukin 2 (IL-2) Biotin MAB (I7663-27M5; L6080803) were from USBiologicals. Sodium chloride (S7653), sodium phosphate dibasic (S0876), sodium phosphate monobasic (S0757), hydrogen peroxide (21676-3), Tween 20 (P9416) and hydrochloric acid (H1758) were from Sigma-Aldrich. 2,2'-Azino-bis(3-ethylbenzthiazoline-6-sulphonic acid) (10102946001) was from Roche.

Particle Preparation

Crosslinked polyethyleneimine particles were prepared according to Example 2, sample G. The only adjustment to a reagent was that the polyethyleneimine solution was adjusted to pH 9 with HCl before dilution to 10%. The experiment was directly scaled by a factor of 4, thus requiring 20 ml mineral oil containing 200 μl of dissolved NP4 with 800 μl of each of the emulsified reactants. The resultant cross-linked polyethyleneimine particles were washed with 6×50 ml of deionised water and recovered by centrifugation at 5000×g for 5 min from the mineral oil and between each wash step. The particle pellet was subsequently resuspended to a volume of 10 ml with deionised water and 500 μl aliquots were used for experiments A to F.

Immobilisation of Proteins

The experiments were assigned letters according to Table 9 below. The addition of the various proteins was carried out in the sequence indicated in the column below the experiment (Table 9). The immobilisation of the first protein component for each experiment was performed in deionised water (sequential addition step 1, Table 9) at 4° C. for 1 hour with inversion of the samples every 10 minutes to ensure adequate mixing. The particles were washed with 3×1 ml of deionised water and recovered as mentioned above.

Subsequent protein binding, the protein treatments (Table 9, rows 2 to 5), were performed in 10 mM phosphate buffer pH 6.8 containing 150 mM sodium chloride (binding buffer). This binding was carried out at 37° C. for 30 minutes with inversion every 5 minutes to ensure adequate mixing. After each protein binding the samples were washed with 2×1 ml of binding buffer containing 0.05% Tween 20 to limit non-specific protein interactions using mild agitation (IKA Vortex Genius, setting 2) for 10 minutes. Recovery of the particles between each successive step was achieved by centrifugation at 5000×g for 5 minutes. The quantity of protein added for each of the protein treatment steps (Table 9) were as follows: albumin—5 mg; rat anti-mouse interleukin 2 MAB (A-IL2-MA)—50 μg; rat anti-mouse IL2 MAB Biotin (B-A-IL2-MA)—25 μg; interleukin 2 (IL-2)—2 ug; streptavidin-peroxidase (strep-perox) 10 μg. These quantities of proteins were prepared in 1 ml of binding buffer.

TABLE 9

Sequence of protein binding for experiments A to F.

| Sequential Addition Step | A | B | C | D | E | F |
|---|---|---|---|---|---|---|
| 1 | A-IL2-MA | A-IL2-MA | IL-2 | Albumin | Albumin | No treatment |
| 2 | Albumin | Albumin | Albumin | — | IL2 | — |
| 3 | — | IL2 | — | — | — | — |
| 4 | B-A-IL2-MA | B-A-IL2-MA | B-A-IL2-MA | B-A-IL2-MA | B-A-IL2-MA | — |
| 5 | Strep-Perox | Strep-Perox | Strep-Perox | Strep-Perox | Strep-Perox | — |

Assay

The peroxidase assay reagent contained 2 mM ABTS and 2 mM hydrogen peroxide in 10 mM phosphate buffer pH 6.8 with 150 mM sodium chloride. Triplicate assays were measured at 420 nm and 30° C. using a Powerwave HT microplate spectrophotometer (Biotek Instruments) with 200 µl of reagent and 50 µl of particle suspension per well.

Results

Figure 12:
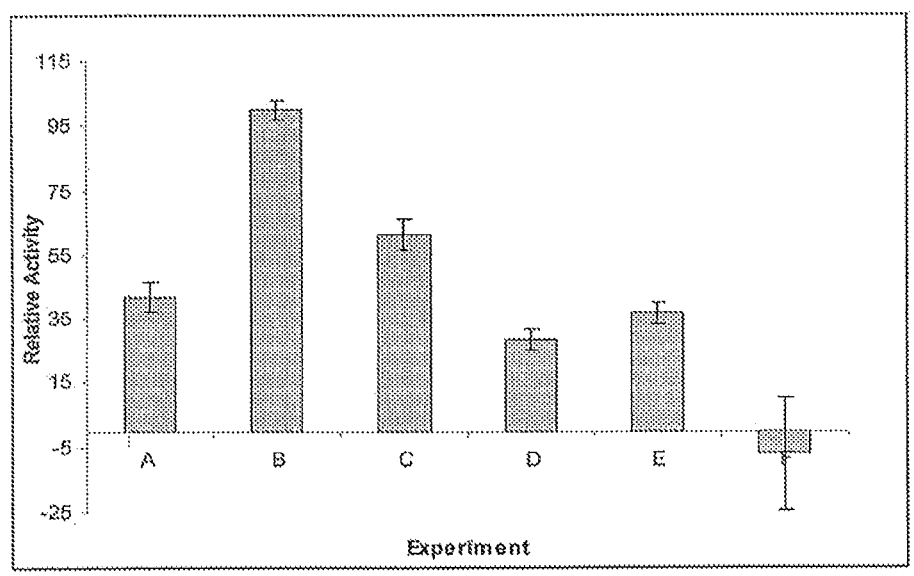
FIG. 12 show the results obtained for peroxidase activity of particles for experiments A to F.

The binding of antibody to antigen was evaluated in Experiment B (FIG. 12). This experiment indicates a positive response which is interpreted as successful binding, of the primary antibody (A-IL2-MA) to the surface of the particles, with successive binding of the antigen (IL-2), secondary antibody (B-A-IL2-MA) and streptavidin-peroxidase to the particles. This is analogous to sandwich ELISA performed on a surface, such as the well of a microtitre plate. Experiment C indicates that an antigen may be bound to the surface of the particles and subsequently used as a recognition element for antibody binding. These experiments, when viewed in comparison with the various controls, indicates that the particles can be used to bind antibody or antigen.

Experiment A is a control to indicate non-specific binding of either the secondary antibody (B-A-IL2-MA) or strepavidin-peroxidase to the particles with immobilised primary antibody. The lower response when compared to B indicates that the antigen (IL-2) enhances binding of the secondary antibody to the particles. Experiment D and E are controls to indicate non-specific binding of primary (A-IL2-MA) or secondary antibody (B-A-IL2-MA) to the particle after albumin quenching. Experiment F contained untreated cross-linked polyethyleneimine particles and was used as an assay control.

This example indicates that the particles are a suitable support immobilisation of antigens or antibodies. We further demonstrate the immobilisation of antibody to antigen and vice-versa through affinity interaction. This example thereby indicates the feasibility of applications of the support for affinity chromatography and diagnostics such as enzyme linked immunosorbent assay.

Example 18

Magnetite Incorporation into Particles of PEI Support Network or Lattice of Polymeric Strands/Fibres The inclusion of mediators and co-factors in the particles has been demonstrated. Inclusion of magnetic particles in the particles is demonstrated in this example.

Particle Preparation

Particles were prepared according to Example 17 above, scaled linearly to 25 ml mineral oil per emulsion. Magnetite (250 mg) was incorporated into the 10% polyethyleneimine liquid solution (pH 9.0) before emulsification. The cross-linked polyethyleneimine particles were washed with 6 volumes 50 ml of deionised water and recovered by centrifugation at 5000×g for 5 min from the mineral oil and between each wash step. The particle pellet was subsequently resuspended to a volume of 10 ml with deionised water and functionalised for anion exchange by reaction with 500 µl of ethylenediamine for 30 minutes. The spheres were subsequently washed with 3×50 ml aliquots of deionised water and recovered by centrifugation as mentioned above. The final pellet was resuspended to 10 ml in deionised water and used for albumin binding experimentation below. The dry weight of the particles was determined in triplicate by lyophilisation and weighing of 1 ml aliquots of the 10 ml particle suspension.

Protein Binding and Quantification

Particles from the aliquots above were recovered by magnetic separation on a magnetic stand (Magnetic Separation Stand—Promega; Z5332) and the liquid removed. Particles were equilibrated with 2×2 ml washes of Tris-Cl buffer, pH 7.4 (50 mM). Bovine serum albumin (BSA) was added to the particles to a final concentration of 20 mg·ml$^{-1}$. Ionic protein binding was allowed to take place for 30 min at room temperature with end-over-end mixing. The mixture was placed in a magnetic stand to retain the magnetised resin on the side wall of the reaction tube and to allow removal of the liquid from the sample. The resin was washed 5 times with 1 ml 50 mM Tris-Cl, pH 7.4 and recovered through the aforementioned magnetic retainer. The ionically bound BSA was eluted from the resin by the addition 2 volumes of 500 µl of 1 M NaCl in 50 mM Tris-Cl, pH 7.4.

Protein Quantification:

Protein quantification of the eluted fraction was performed on a Qubit Fluorometer (Invitrogen) using the Quant-iT assay as per the manufacturer's instructions (Table 10).

Results

TABLE 10

Binding of albumin to magnetite containing particles (averages of triplicate data).

| Particle Dry Weight (mg) | Protein Binding (mg) | Binding Efficiency (% m/m) |
|---|---|---|
| 31.58 ± 0.90 | 1.07 ± 0.01 | 3.39 |

The results indicate that magnetite may be incorporated into the particles and the magnetic properties of the particles may be used for effective separation of these from a liquid suspension. Further, these results indicate that the support may be used as an efficient ion exchange resin. In the example provided here the modification of the particle matrix with a positively charged molecule such as an amine (ethylenediamine) allows the use of the particles as an anion exchange resin. The use of negatively charged molecules such as carboxyl containing molecules would allow use as a cation exchange resin.

This example further provides an example of an alternative recovery method by inclusion of magnetic particles into the lattice, which would allow them to be attracted through application of a magnetic field.

The particles of the invention thus include lattices of polymeric strands or fibres cross-linked by means of a cross-linking agent, and interstitial openings or spaces adjacent and around the fibres. In other words, the invention provides a fibrous interpenetrating network particle, preferably constructed or made up from glutaraldehyde cross-linked polyethyleneimine. The particle may be applied as an enzyme immobilisation matrix.

The particles are preferably produced using the emulsion based technology or techniques of the second and third aspects of the invention. The use of an emulsion based technology allows for the benefits of size control such as the control of particle surface area to volume ratio and defined size distribution, and also advantageously permits a single step synthesis of the particles. The particles offer a large surface area for immobilisation and are applicable to, but not limited to, biocatalysis of large and small substrates. This enzyme immobilisation matrix exhibits a high immobilisation efficiency and high enzyme activity maintenance after immobilisation.

The fibrous nature of the dendritic particles provides a large internal surface area for enzyme binding. Also, the large number of available attachment points per enzyme subunit provides for the opportunity of significantly improved protein stabilization, when compared to the backbone support material, eg PEI, on its own. This, combined with the loose lattice or network, allows for a high activity to weight ratio after biocatalyst addition due to the large exposed surface area for immobilisation and limited diffusional constraints for small and large substrates. Furthermore, control of particle size allows for increased reduction for diffusional constraints of the substrates should this be a hindrance of this immovilisation matrix.

The process of preparation of the particles includes the emulsification of the backbone support or lattice with or without the cross-linking agent in the same phase. Preferably a bi-emulsion system is used for the manufacture, as hereinbefore described. In the case where the cross-linking agent is not included in the first emulsion, it may be dissolved in the oil phase, or be incorporated by mixing a second emulsion containing said cross-linking agent.

The preferred process of manufacture is separate emulsification of the backbone polymer (polyethyleneimine) in an emulsion with an at least bifunctional cross-linking chemical (glutaraldehyde) in a second emulsion. The spontaneous reaction between the polymer and cross-linking agent results in a fibrous lattice or network, containing in this case, excess aldehyde functional groups, which are subsequently used to spontaneously covalently link proteins to the lattice or support through amine-aldehyde cross-reactivity. This aldehyde functionality can further be extrapolated to link alternative compounds, or to impart other properties such as hydrophobicity, thereby expanding its application to binding a broader range of proteins, such as hydrophobic proteins.

Protein immobilisation to matrices enhances the solvent, thermal and pH stabilities of the enzymes. This stabilization may further be enhanced by drying the support after protein immobilisation to the dendritic support. It is believed that this drying reduces the proximity of cross-reactive chemical functional groups, thereby eliciting further spontaneous chemical coupling of protein-backbone and backbone-backbone. Furthermore, additives may be entrapped in the matrix during drying which could be of useful for control of pore size or entrapment of functional molecules or adjunct. High protein loadings are possible with the particles of the invention i.e. relatively large quantities of protein can be loaded in a small particle volume.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

That which is claimed:

1. A process for producing particles, which includes allowing, in an emulsion, across-linking agent to cross-link polyethyleneimine strands, thereby forming particles, each particle comprising a lattice of the polyethyleneimine strands cross-linked by means of the cross-linking agent, interstitial openings adjacent and around the polyethyleneimine strands, and aldehyde functional groups on the lattice with which proteins and/or modified proteins can react, thereby to be bonded to the lattice and hence immobilized, with the particles hence being emulsion derived.

2. A process according to claim 1, wherein the polyethyleneimine and the cross-linking agent are present in a dispersed phase of the emulsion.

3. A process according to claim 1, wherein the cross-linking agent is present in a continuous phase of the emulsion.

4. A process according to claim 1, wherein the polyethyleneimine and cross-linking agent are provided in separate dispersed phases in the emulsion.

5. A process according to claim 1, wherein the polyethyleneimine and cross-linking agent are mixed prior to dispersion in a continuous phase of the emulsion.

6. A process according to claim 1, which includes adding an adjunct to at least one phase of the emulsion, so that the adjunct is entrapped within the lattices of the particles.

7. A process according to claim 1, which includes recovering the particles and drying the recovered particles.

8. A process according to claim 7, which includes adding an adjunct to the recovered particles before the drying of the particles, so that the adjunct becomes entrapped within the lattices of the particles.

9. A process for producing particles, which includes allowing, in an emulsion, a cross-linking agent to cross-link polyethyleneimine strands, thereby forming particles, each particle comprising a support lattice of the polyethyleneimine strands cross-linked by means of the cross-linking agent, with the polyethyleneimine strands thus forming a network backbone of the support lattice, interstitial openings adjacent and around the strands, and aldehyde functional groups on the support lattice with which proteins and/or modified proteins can react, thereby to be bonded to the support lattice and hence immobilized, with the particles hence being emulsion derived.

\* \* \* \* \*

UNITED STATES PATENT AND TRADEMARK OFFICE
CERTIFICATE OF CORRECTION

PATENT NO. : 9,574,054 B2  
APPLICATION NO. : 14/945002  
DATED : February 21, 2017  
INVENTOR(S) : Jordaan et al.

Page 1 of 1

It is certified that error appears in the above-identified patent and that said Letters Patent is hereby corrected as shown below:

In the Claims

Column 26, Claim 1, Line 9:
Please correct "emulsion, across-linking agent" to read -- emulsion, a cross-linking agent --

Signed and Sealed this  
Tenth Day of October, 2017

Joseph Matal  
*Performing the Functions and Duties of the*  
*Under Secretary of Commerce for Intellectual Property and*  
*Director of the United States Patent and Trademark Office*